US008886332B2

(12) United States Patent
Molnar et al.

(10) Patent No.: US 8,886,332 B2
(45) Date of Patent: Nov. 11, 2014

(54) VISUALIZING TISSUE ACTIVATED BY ELECTRICAL STIMULATION

(71) Applicant: Medtronic, Inc., Minneapolis, MN (US)

(72) Inventors: Gabriela C. Molnar, Fridley, MN (US); Maciej T. Lazarewicz, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/826,837

(22) Filed: Mar. 14, 2013

(65) Prior Publication Data

US 2013/0289660 A1 Oct. 31, 2013

Related U.S. Application Data

(60) Provisional application No. 61/638,801, filed on Apr. 26, 2012, provisional application No. 61/648,655, filed on May 18, 2012.

(51) Int. Cl.
A61N 1/05 (2006.01)
A61B 5/00 (2006.01)
A61B 5/04 (2006.01)
A61N 1/372 (2006.01)
A61N 1/36 (2006.01)

(52) U.S. Cl.
CPC .......... *A61B 5/4893* (2013.01); *A61N 1/36185* (2013.01); *A61B 5/7225* (2013.01); *A61B 5/742* (2013.01); *A61B 5/04001* (2013.01); *A61N 1/37247* (2013.01); *A61N 1/3605* (2013.01); *A61B 5/7475* (2013.01); *A61N 1/36146* (2013.01); *A61N 1/36182* (2013.01); *A61B 5/4836* (2013.01)
USPC .......................................................... 607/59

(58) Field of Classification Search
None
See application file for complete search history.

(56) References Cited

U.S. PATENT DOCUMENTS

| 7,346,382 | B2 | 3/2008 | McIntyre et al. |
| 7,822,483 | B2 | 10/2010 | Stone et al. |
| 7,860,548 | B2 | 12/2010 | McIntyre et al. |
| 8,190,250 | B2 | 5/2012 | Moffitt et al. |
| 2007/0083104 | A1 | 4/2007 | Butson et al. |
| 2007/0203540 | A1 | 8/2007 | Goetz et al. |
| 2007/0276234 | A1 | 11/2007 | Shahidi |

(Continued)

FOREIGN PATENT DOCUMENTS

| WO | 2007097858 A1 | 8/2007 |
| WO | 2008070140 A2 | 6/2008 |

(Continued)

OTHER PUBLICATIONS

Boston et al., "Sources and Effects of Electrode Impedance During Deep Brain Stimulation," Clinical Neurophysiology, 117, Dec. 22, 2005, 8 pp.

(Continued)

*Primary Examiner* — Paula J Stice
(74) *Attorney, Agent, or Firm* — Shumaker & Sieffert, P.A.

(57) ABSTRACT

A visualization of an area or volume of tissue activated during stimulation according to a set of stimulation parameters is generated. The area or volume of activation is modeled based on a non-uniform grid of model neurons. Select portions of the grid have the model neurons more closely spaced, resulting in finer resolution graphical representation, while less closely spaced model neurons in other portions of the grid may avoid additional computation time.

25 Claims, 17 Drawing Sheets

(56) References Cited

U.S. PATENT DOCUMENTS

| | | |
|---|---|---|
| 2007/0288064 A1* | 12/2007 | Butson et al. ............... 607/45 |
| 2008/0154341 A1* | 6/2008 | McIntyre et al. ............ 607/59 |
| 2009/0208073 A1 | 8/2009 | McIntyre et al. |
| 2009/0287271 A1 | 11/2009 | Blum et al. |
| 2010/0049276 A1* | 2/2010 | Blum et al. ............... 607/45 |
| 2011/0040351 A1 | 2/2011 | Butson et al. |
| 2011/0093044 A1 | 4/2011 | Moffitt |
| 2011/0093045 A1 | 4/2011 | Moffitt et al. |
| 2011/0191275 A1 | 8/2011 | Lujan et al. |
| 2011/0307032 A1 | 12/2011 | Goetz et al. |

FOREIGN PATENT DOCUMENTS

| | | | |
|---|---|---|---|
| WO | 2009137120 A1 | 11/2009 | |
| WO | 2010120823 A2 | 10/2010 | |
| WO | 2011025865 A1 | 3/2011 | |

OTHER PUBLICATIONS

McIntyre et al. "Cellular Effects of Deep Brain Stimulation: Model-Based Analysis of Activation and Inhibition," J Neurophysiol, vol. 91, pp. 1457-1469, 2004 (First published Dec. 10, 2003).

U.S. Appl. No. 13/826,448, by Gabriela C. Molnar, filed Mar. 14, 2013.

Invitation to Pay Fees from International Application No. PCT/US2013/034583, dated Jan. 8, 2014, 6 pp.

International Search Report and Written Opinion from International Application No. PCT/US2013/034583, 14 pp.

* cited by examiner

VISUALIZING TISSUE ACTIVATED BY ELECTRICAL STIMULATION

This application claims the benefit of U.S. Provisional Application No. 61/638,801, filed on Apr. 26, 2012 and entitled, "VISUALIZING TISSUE ACTIVATED BY ELECTRICAL STIMULATION," and the benefit of U.S. Provisional Application No. 61/648,655 filed May 18, 2012 and entitled "TECHNIQUES FOR DETERMINING VOLUME OF TISSUE ACTIVATED", the entire content of each of which is incorporated herein by reference.

TECHNICAL FIELD

The disclosure relates to electrical stimulation therapy and, more particularly, visualization of tissue activated by electrical stimulation.

BACKGROUND

Medical devices, such as electrical stimulators, may be used in different therapeutic applications, such as deep brain stimulation (DBS), spinal cord stimulation (SCS), pelvic stimulation, gastric stimulation, peripheral nerve stimulation, cardiac rhythm management, and functional electrical stimulation. A medical device may be configured to deliver therapy to a patient to treat a variety of symptoms or patient conditions such as chronic pain, tremor, Parkinson's disease, other types of movement disorders, seizure disorders (e.g., epilepsy), urinary or fecal incontinence, sexual dysfunction, obesity, mood disorders, gastro paresis or diabetes. For example, an IMD may deliver an electrical stimulation therapy such as cardiac pacing, cardiac cardio version/defibrillation, neurostimulation, muscle stimulation, or the like.

An implantable medical device may provide electrical stimulation therapy according to a set of stimulation parameter values, which may also be referred to as a therapy program. A therapy program may define respective values for each of a plurality of electrical stimulation parameters, e.g., as specified by a clinician. In some cases, the medical device may receive one or more therapy programs from an external medical device programmer operated by the clinician. In addition, in some cases, a patient also may be equipped with a medical device programmer and may interact with the programmer to select or modify therapy programs for delivery of stimulation.

Examples of implantable medical devices that deliver electrical stimulation include implantable neurostimulators, implantable cardioverters, implantable cardiac pacemakers, implantable cardioverter-defibrillators, and cochlear implants. Such devices may be implanted or external to a patient, and configured to deliver electrical stimulation therapy to and/or measure a signal from a target tissue site within the patient. The electrical stimulation may be delivered to the tissue site via electrodes, some of which may be located on a device housing and/or on one or more implantable leads.

SUMMARY

In general, the disclosure is directed to providing a user with a graphical visualization of the tissue activated by electrical stimulation delivered according to a set of stimulation parameter values applied via one or more electrodes. In some examples, the graphical visualization may help a user program stimulation parameters for electrical stimulation therapy delivered by an electrical stimulator. For example, the user may interact with a computing device presenting a graphical representation of an area of tissue activated by electrical stimulation (also referred to herein as an "activated tissue area") to define a desired area of tissue activation. A visualization of the extent of tissue activation produced by the electrical stimulation may help a user determine whether the selected stimulation parameter values provide a desired activation, e.g., stimulation within a particular region of tissue without significantly activating neighboring tissue regions.

In some examples, a computing device is configured to generate and display more than one version of the graphical representation of the activated tissue area. The different versions may correspond to different fiber orientations, where the fiber may be, for example, a nerve fiber or axon. The sensitivity of a neuron to electrical stimulation may depend on the fiber orientation. In addition, the shape and size of the VTAs change based on fiber orientation, it may be useful to incorporate information about fiber direction. The display of different versions of the activated tissue area for a particular set of therapy parameter values may allow for the user to consider a range of possible areas of activation. Based on the one or more displayed graphical representations of activated tissue areas, the user may decide whether to modify the set of parameter values to provide a different area of activation.

In some examples, visualization of the extent of activation of tissue resulting from delivery of electrical stimulation according to a set of stimulation parameter values may be generated based on a non-uniform grid of neuron representatives. The use of a non-uniform grid as a framework from which to generate a visualization of an activated area can allow for a balance between computation time and image resolution by replacing a portion of a uniform grid having a coarse spacing with a portion of finely spaced neuron representatives. In some examples, the portion of the grid that includes finely spaced neuron representatives is near an edge of an activation area where finer resolution may make a difference in the graphical representation presented to a user. In one example, the neuron representatives are oriented perpendicular to a longitudinal axis of the lead and the locations of the neuron representatives constitute a grid. In other examples, the neurons representatives may be oriented at various angles between 0 and 90 degrees with respect to a longitudinal axis of the lead. In other examples, the neuron representatives may be have an orientation that is not straight but follows an anatomically realistic pathway with respect to a longitudinal axis of the lead.

For each neuron representative within a first uniform grid, the processor may determine an activation threshold value, which may be the threshold value (e.g., an amplitude or intensity value) at which the neuron representative is activated. The processor may compare the activation threshold values of adjacent neuron representatives and, based on the comparison, determine whether to add an additional grid point between the adjacent neuron representatives of the grid. For example, the processor may add additional grid points in areas in which adjacent neuron representatives have significantly different threshold values. In one example, an additional grid point may be added when one of the neuron representatives has an activation threshold value below a predetermined value, and the difference between the threshold values of the two neuron representatives is greater than twice the predetermined value.

In some examples, a computing device may generate a visualization, or representation, of the extent of activation of tissue that would result from delivery of stimulation according to a particular set of stimulation parameter values using a non-uniform grid. A computing device can determine whether each individual neuron representative would be activated based on the stimulation parameter values. The processor may then use the state of each neuron representative (activated or not) to generate a visualization of an activation area. The activation area may be an activation contour if the visualization is a two-dimensional (2D) image. The activation area may be an activation volume if the visualization is a three-dimensional (3D) image.

In some examples, a method comprises receiving, with one or more processors, a therapy delivery element selection, wherein the therapy delivery element selection corresponds to a therapy delivery element selected for implantation in a patient; receiving, with the one or more processors, a set of therapy parameter values. The method also includes retrieving, from a memory, an area of activation look-up table based on the therapy delivery element selection, the area of activation look-up table comprising a neuron representative grid, wherein each neuron representative of the neuron representative grid is associated with a plurality of activation thresholds, each threshold of the plurality of activation thresholds being associated with an angle of rotation around an axis, and wherein thresholds of the plurality of activation thresholds are organized into a plurality of activation threshold sets. In addition, the method includes generating, with the one or more processors, a plurality of areas of activation based on the set of therapy parameter values, wherein each area of activation is generated based on a different threshold set of the plurality of activation threshold sets.

In some examples, a system includes a memory and a processor. The memory is configured to store a plurality of areas of activation look-up tables, the plurality of look-up tables being associated a therapy delivery element selection. The processor is configured to receive a therapy delivery element selection, wherein the therapy delivery element corresponds to a therapy delivery element selected for implantation in a patient, receiving a set of therapy parameters; retrieve, from the memory, an area of activation look-up table from the plurality of areas of activation look-up tables based on the therapy delivery element selection, wherein the area of activation look-up table comprises a neuron representative grid, and wherein each neuron representative of the neuron representative grid is associated with a plurality of activation thresholds, each threshold of the plurality of activation thresholds being associated with an angle of rotation around an axis, and wherein the thresholds of the plurality of activation thresholds are organized into a plurality of threshold sets, and generate a plurality of areas of activation based on the set of therapy parameter values, wherein each area of activation is generated based on a different threshold set of the plurality of activation threshold sets.

In some examples, a system includes means for receiving a therapy delivery element selection, wherein the therapy delivery element selection corresponds to a therapy delivery element selected for implantation in a patient; means for receiving a set of therapy parameters; means for retrieving, from a memory, an area of activation look-up table based on the therapy delivery element selection, wherein the area of activation look-up table comprises a neuron representative grid, and wherein each neuron representative of the neuron representative grid is associated with a plurality of activation thresholds, each of the plurality of activation thresholds associated with an angle of rotation around an axis, and wherein the plurality of activation thresholds are organized into a plurality of threshold sets; and means for generating a plurality of areas of activation based on the set of therapy parameters, wherein each area of activation is generated based on a different threshold set.

In some examples, a computer readable storage medium comprising a set of instructions, the set of instructions causing a programmable processor to receive a therapy delivery element selection, wherein the therapy delivery element selection corresponds to a therapy delivery element selected for implantation in a patient; receive a set of therapy parameters; retrieve, from a memory, an area of activation look-up table based on the therapy delivery element selection, wherein the area of activation look-up table comprises a neuron representative grid, and wherein each neuron representative of the neuron representative grid is associated with a plurality of activation thresholds, each of the plurality of activation thresholds associated with an angle of rotation around an axis, and wherein the plurality of activation thresholds are organized into a plurality of threshold sets; and generate a plurality of areas of activation based on the set of therapy parameters, wherein each area of activation is generated based on a different threshold set.

The details of one or more examples are set forth in the accompanying drawings and the description below. Other features, objects, and advantages will be apparent from the description and drawings, and from the claims.

DETAILED DESCRIPTION

Figure 1:
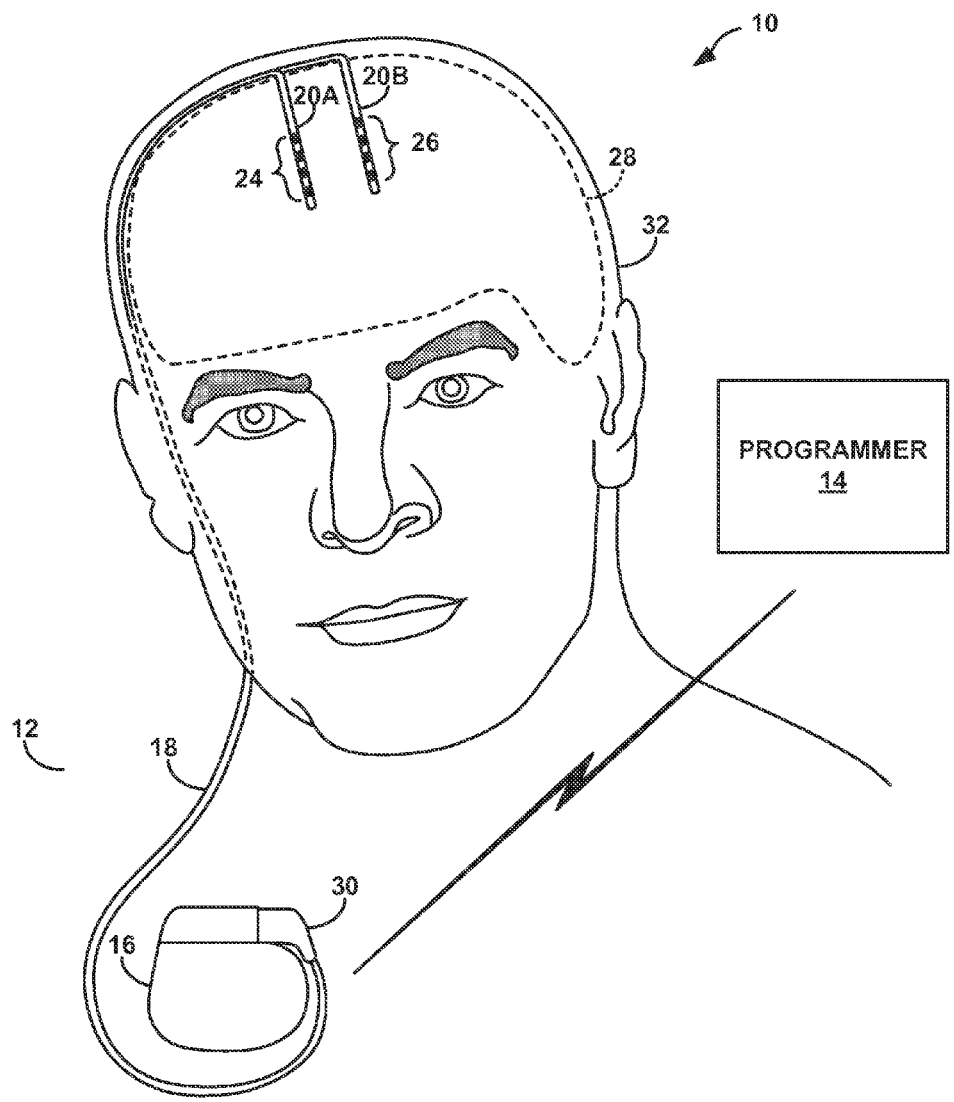
FIG. 1 is a conceptual diagram illustrating an example therapy system configured to deliver therapy to a patient to manage a patient condition.

This disclosure describes devices, systems, and techniques for generating a graphical representation of an area (e.g., an activation contour or volume) of tissue that is expected to be activated, e.g., based on one or more tissue activation models, if electrical stimulation is delivered to a target tissue location with specified electrical stimulation parameter values. The electrical stimulation parameters may define an aspect of the electrical stimulation therapy, and may include, for example, an electrode combination (e.g., selected electrodes and associated polarities), voltage or current amplitude of an electrical stimulation signal, a charge level of an electrical stimulation, a frequency of the electrical stimulation signal, and, in the case of electrical stimulation pulses, pulse rate, pulse width, waveform shape, and other appropriate parameters such as duration or duty cycle. In some examples, stimulation may be delivered using a continuous waveform and the stimulation parameters may define this waveform. The stimulation amplitude may be a controlled current or a controlled voltage amplitude. Stimulation parameter values may include, for example, a pulse width, ranging from approximately 60 μsec to approximately 450 μsec, and an amplitude ranging from approximately 0 milliamps (mA) to approximately 100 mA.

In some examples, a computing device is configured to generate and display the graphical representation of the area of tissue that is expected to be activated if electrical stimulation is delivered to a target tissue location with specified electrical stimulation parameter values. The stimulation parameters may include, for example, amplitude and pulse width of the applied stimulation, as well as an electrode combination for delivery of the stimulation pulse. In some systems that deliver stimulation based on a level of charge (e.g., a charge per stimulation pulse) rather than pulse width and amplitude, the stimulation parameters may include this charge level. This area of tissue may also be referred to as an "activation area." The graphical representation may also include one or more of a representation of a therapy element (e.g., a lead, a catheter carrying one or more electrodes, or a leadless stimulator), a depiction of one or more electrodes, and an indication as to which of the electrodes are being used to provide stimulation. In addition, in some examples, the graphical representation may include a graphical representation of an activation area (e.g., volume or activation contour) derived from tissue activation modeling calculations based on a non-uniform grid of neuron representatives. As used herein, the non-uniform grid refers to a grid of neuron representatives with unequal spacing between neuron representatives. In some examples, the activation area that is generated in the graphical representation may be displayed along with one or more anatomical brain structures, e.g., obtained from an anatomical atlas or a radiological image.

As described in more detail below, the use of a uniform grid may result in a graphical representation of an activation contour that is not accurate. For example, an activation contour generated using a uniform grid may include a sharp cutoff between two portions of the activation contour. However, the use of a non-uniform grid may allow for greater resolution, and more gradual sloping to areas of the activation contour.

In some examples described herein, a processor (e.g., of a medical device programmer or another computing device) is configured to generate an activation area, e.g., an activation contour or activation volume, for a plurality of sets of stimulation parameter values. In some examples, the amplitudes of the sets of stimulation parameter values with which the processor generates the activation areas may be limited by the programmable range of the implantable medical device (IMD) that will be providing (e.g., generating) the stimulation. For example, the stimulation amplitude range for some IMDs configured to deliver deep brain stimulation (DBS) may be between approximately 0 and 25.5 milliamps (mA) or between approximately 0 and 10.5 volts (V). In some examples the stimulation amplitude range may be between approximately 0 and 10 mA. In examples in which the sets of stimulation parameter values include pulse width values, the pulse width may also vary over a range, for example, from approximately 60 to 450 microseconds (μsec).

In some examples, a user such as a clinician or other caregiver, e.g., via a user interface of a computing device, may select stimulation parameter values to model the effects of stimulation, and, based on the input, the processor of the computing device may generate and display one or more activation areas. The stimulation parameter values may include selection of an electrode configuration (also referred to herein as an "electrode combination"), e.g., which electrodes of a plurality of electrodes are providing the stimulation and associated electrode polarities (e.g., positive polarity, negative polarity, or inactive electrode).

A particular lead or other therapy delivery element that is implanted with in the patient may also have a defined electrode spacing or shape. For example, a first lead may have electrodes approximately 1.5 millimeters (mm) long and spaced 1.5 mm apart while a second lead may have electrodes 1.5 mm long and spaced 0.5 mm apart. In some examples, the user may provide input to the computing device indicating a configuration of the one or more therapy delivery elements implanted within the patient, and, based on the input, the processor of the computing device may generate and display one or more activation areas. The user may, for example, provide input that indicates a type of lead implanted in the patient, and the processor may provide a visualization of tissue activation area based on the type of lead. In some examples, more than one lead may be implanted, each lead having a plurality of electrodes. Each electrode may be combined with any other electrode on the same lead or on a different lead to define an electrode configuration. In some examples, a user may provide input to the computing device that indicates which electrodes are selected to provide electrical stimulation. The electrodes may define a monopolar, bipolar or multipolar configuration. In one example, a configuration can be considered monopolar or unipolar if an electrode on an electrical stimulator housing is programmed as the anode and one or more electrodes on the lead are programmed as cathodes.

In some examples, after the stimulation parameter values have been chosen by a user, including which electrodes are providing the stimulation, the processor generates a grid, with which the processor may determine one or more activation areas. In some examples, the grid is defined by neuron representatives. Each neuron representative may be presented as a dot when a visual representation of the grid is displayed by the processor, where each dot represents the center of a respective neuron representative or model neuron.

Each neuron representative is associated with a threshold value of activation (also referred to herein as an "activation threshold value" or "activation threshold"). The threshold value for each neuron representative may be obtained using a binary search algorithm. The threshold value is a stimulation voltage or current amplitude, that when applied to an actual neuron of the type being modeled, results in a propagating action potential along the neuron. In some examples, the action potential is considered to have excited, or "activated", the neuron representative if the transmembrane potential reached a threshold greater than 0 mV. As used herein, the threshold value of activation may be referred to as a threshold, an activation threshold, or a propagation threshold.

In some examples, the processor may model the neuron representatives as multi-compartment cables with non-linear membrane mechanisms that include fast and persistent sodium, potassium and leakage conductances. In some examples, the axon may be modeled to include a number of nodes. In some examples, each axon is modeled with 21 nodes of Ranvier for single cathode monopolar stimulation modules, and with 71 nodes of Ranvier for other electrode combinations. In another example, each axon is modeled with 111 nodes of Ranvier. Other models may be used in the alternative.

In some examples, the processor runs a neuron modeling program that monitors the voltage at the penultimate node of the neuron representative to determine if the transmembrane potential is greater than 0 mV. The amplitude that results in a transmembrane potential greater than 0 mV is the activation threshold. For example, for a 5.7 µm-diameter neuron, the current amplitude resulting in a transmembrane potential greater than 0 mV may be in a range of approximately 0.1 to approximately 25 mA for neuron locations of interest. IN some examples, the activation threshold may be a charge level that results in a transmembrane potential greater than 0 mV. The activation threshold value will vary depending on the location and orientation of the modeled neuron relative to the active electrodes, as well as with the electrical properties of the tissue surrounding the electrodes, and stimulation parameter values.

In some examples, the neuron representatives in a grid may be associated with different activation thresholds, which may better represent the neurons at the target tissue site for the electrical stimulation therapy. A particular neuron type in one part of the patient's body (e.g., in one part of the brain) may require a different current to generate a propagating action potential than another neuron type in the same or different part of the brain, or the same neuron type in a different part of the body (e.g., in a different part of the brain). In addition, in some examples, the lead may be placed in a location where more than one neuron type is present. Thus, in some examples, a processor may change the activation threshold value associated with each neuron representative based on the location at which the stimulation is intended to be applied. The processor may make the modification, for example, based on user input, or based on information stored in a memory. The grid may have neuron representatives with different activation threshold values mixed within the grid to simulate the interconnection of different neuron types in the part of the body (e.g., the brain) intended to be stimulated.

The location of implantation of the lead may also result in differences in neuron orientation with respect to the lead. The sensitivity of a neuron to electrical stimulation may depend upon the neuron's orientation (fiber orientation) with respect to the lead due to the relationship between conductivities/anisotropy and neuron fiber directionality. In addition the shape and size of the area of activation changes based on fiber orientation. In some examples, the area surrounding the lead may include neurons with multiple different fiber orientations. Accordingly, the neuron representatives of the grid may be associated with one or more fiber orientations. In some examples, a processor generates one or more area of activations representing one or more possible fiber orientations at the area of implantation.

In some examples, each of the neuron representatives of a grid may have a fiber orientation (also referred to as "fiber direction"). The fiber orientation dictates the direction of propagation of an action potential for an activated neuron representative. In some examples, each of the neuron representatives of a grid has the same fiber orientation such as substantially perpendicular (e.g., perpendicular or nearly perpendicular) to a longitudinal axis of a lead representative. In some examples, each of the neuron representatives of a grid has a different fiber orientation with respect to a longitudinal axis of a lead representative (e.g., some neuron representatives are perpendicular, some neuron representatives are parallel).

In some examples, each of the neuron representatives of a grid consists of an anatomically reconstructed fiber pathway. In some examples, the processor may select or change the fiber orientation of the neuron representatives with respect to the longitudinal axis of the lead representative to match the average orientation of neurons in the tissue surrounding an implanted lead for which stimulation is being modeled. The processor may determine the fiber orientation for a neuron representative using any suitable technique. For example, the processor may determine the fiber orientation based on a diffusion tensor image (DTI) or another type of medical image of the patient that may provide a graphical representation of the axonal pathways of the regions of interest of the patient's body. The use of DTI or fiber tracking, for example, may result in additional, patient specific, computational analysis in order to generate patient-specific areas of activation. In other examples, a generic fiber atlas or prior knowledge of anatomy in the desired area may be used to indicate the direction of fiber pathways near the lead and electrodes. In some examples, fiber orientations associated with each point of the grid of neuron representatives may be different depending on the location of the lead. For example, if the lead is close to an internal capsule, neuron representatives close to the lead may indicate the direction of capsular fibers. If the lead is farther from the internal capsule, the neuron representatives assigned with the capsular fiber directionality may be at a different location within the grid. As another example, the processor may determine the fiber orientation based on user input. In some examples, the processor is configured to present a user interface that enables a user to toggle between a subset of fiber orientations, e.g., fibers oriented parallel to the lead or perpendicular to the lead. In some examples, the processor may simultaneously display activation areas corresponding to multiple fiber orientations.

In some examples, the processor runs simulations to determine a plurality of activation thresholds for each neuron representative, e.g., prior to receiving stimulation parameter values from a user. For example, the processor may run multiple simulations for each possible electrode combination at each of a plurality of pulse widths to determine the threshold current amplitude needed to activate each neuron representative of a grid for the respective pulse width. For example, the processor may generate a grid of neuron representatives and activation thresholds for pulse widths of 60 μsec, 90 μsec, 150 μsec, 210 μsec, 330 μsec, and 450 μsec. In modeling the neuron representative grid, the processor may assign each of the active electrodes a conductivity corresponding to the conductivity of the material used for the therapy delivery device (e.g., a lead) being modeled. For example, the processor may assign each active electrode a conductivity of platinum (9.3e6 Siemens per meter (S/m)), and assign insulation between the active electrodes a conductivity of 0.001 S/m. In some examples, the processor assigns non-active electrodes the same conductivity as the insulation. In addition, in some examples, the modeling of the lead may also include a lead encapsulation 0.5 mm thick with a conductivity of 0.1 S/m. The lead encapsulation may surround the entire lead. In some examples, the computer model of the medium surrounding the lead may be a cylinder with a radius of 50 mm and a height of 100 mm.

In some examples, for each of the plurality of pulse widths being modeled, each of the neuron representatives may be associated with a plurality of activation threshold values, where each threshold of the plurality of activation thresholds may correspond to a different fiber orientation. For example, each neuron representative may have 10 activation thresholds associated with it in a look-up table for each pulse width of a plurality of pulse widths. Depending on the way the stimulation parameters are defined (e.g., amplitude and pulse width versus charge level and pulse shape), each neuron representative may have an activation threshold for each fiber orientation for each stimulation parameter value of a plurality of stimulation parameter values. In some examples, each of the activation thresholds is associated with a respective angle, e.g., determined from 0 degrees through 90 degrees at 10 degree increments. The shape and size of the activation areas may change based on fiber orientation. Thus, it may be useful to simulate and display different activation areas based on different fiber orientations to give the user a robust visualization of the activation area that may result from a particular set of stimulation parameter values.

In some examples, a processor generates a list in which a plurality of thresholds associated with a particular neuron representative are grouped or ranked from the lowest to highest threshold. For example, the processor may generate a list of ten Groups, where, in rank order, Group 1 may correspond to the fiber orientations resulting in the lowest relative activation thresholds for the neuron representatives, and Group 10 may correspond to the fiber orientations resulting in the highest thresholds for the neuron representatives, and Groups 2-9 may correspond to fiber orientations that result in activation thresholds in between the lowest and the highest activation thresholds. In other examples, the groupings may include activation thresholds associated with the same fiber orientation. For example, in rank order, Group 1 may correspond to the activation thresholds of neuron representatives having fibers oriented parallel to the longitudinal axis of the lead, while Group 10 may correspond to the activation thresholds of neuron representatives having fibers oriented perpendicular to the longitudinal axis of the lead, and Groups 2-9 may correspond to angles between the parallel and perpendicular axon orientations.

In some examples, in order to determine how closely to locate the neuron representatives to one another in the grid, a processor estimates the electric field gradient (e.g., sometimes also called the "activating function") generated by a stimulation pulse according to a selected set of stimulation parameter values. Based on the intensity of strength of the electric field gradient, the processor places neuron representatives within the grid using at least two different spacings. For example, in the area where the electric field gradient is near zero, the processor may use a first, smaller, spacing between adjacent neuron representatives. That is, the neuron representatives in the area with the relatively low electric field gradient strength may be closer together within the grid than the neuron representatives in the areas with an electric field gradient strength above the electric field gradient threshold.

In some examples the electric field gradient threshold with which the processor determines the grid spacing is zero. That is, at any place that the electric field gradient strength is zero, the neuron representatives are relatively closely spaced compared to the neuron representatives in areas with a strong electric field gradient strength. In some examples, the electric field gradient threshold is above zero. The processor may select the electric field gradient threshold using any suitable criteria, e.g., based on a balance between a desire for a more detailed final graphical representation and the time it takes to generate the graphical representation. In general, the higher the electric field gradient threshold, the more area that is under the electric field gradient threshold. A processor may generate a grid including more neuron representatives for relatively higher electric field gradients. In turn, this results in more computations to determine whether each of the neuron representatives is activated by the stimulation. The inclusion of more neuron representatives in a grid also results in a greater part of the graphical representation having finer resolution.

In some examples, in order to determine the location of neuron representatives for a particular lead and electrode combination, a processor calculates a field solution using the Laplace equation. The field solution is the distribution of voltages within the medium surrounding the lead (e.g., gray matter). In some examples, the processor assigns a voltage of 0V to the outer boundary of the cylinder used in the simulation of a cathode or double cathode stimulation. The processor may assign a voltage of −1V to cathode(s) in the simulation and 0V to the anode(s) in the simulation. The processor may use the field solution to determine activation thresholds for each of the neuron representatives of an initial grid of neuron representatives for a particular pulse width. After the processor determines the activation thresholds for the initial grid of neuron representatives, the processor compares the activation thresholds of adjacent neuron representatives, and if the difference between the two thresholds is above a predetermined level, the processor may add an addition neuron representative in between the two neuron representatives that the processor compared. In some examples, the process of comparing thresholds may be repeated until no additional neuron representatives are needed.

In some examples, the grid is a 2D grid. The 2D grid may be used to generate an activation contour. In some examples, the activation contour indicates the tissue activation in a plane defined by a Z-axis and a Y-axis, with the longitudinal axis of the lead representative on the Z axis. In some examples, the processor may replicate the activation contour at a plurality of rotational positions, e.g., evenly spaced about the available 360 degrees, around the lead representative in order to create a 3D graphical representation depicting an activation volume. In other examples, the processor generates a 3D grid and generates an activation volume based on the 3D grid. In some examples, a 3D grid may consist of multiple 2D grids rotated around the longitudinal axis of a lead representative. The 3D grid may be used if there are non-symmetrical electrodes on a lead (e.g., in one example, if the ring electrodes are partitioned into two or more electrode segments).

In some examples, the grid may be associated with at least one electrode selected to apply electrical stimulation. For example, a grid may be generated to model stimulation provided by a therapy delivery element such as a leadless stimulator. In such examples, a lead representative may not be present. In some examples, electrodes may be on a catheter, instead of a lead. In such examples, a catheter representative may be used instead of a lead representative.

After the grid has been generated, a processor determines which of the neuron representatives is activated at a specific pulse width. This determination may be based on characteristics of the electrical field, the activation threshold value for propagation (activation) for the neuron representatives, and the fiber orientation. The processor may select neuron representatives that are at the edge of the activation area to create the edge of the activation contour or activation volume. In other cases, linear interpolation of the threshold values of the neuron representatives located at each point on the grid may be used to generate the approximate contour for a user-specified amplitude and pulse width combination. In some examples, the use of the non-uniform grid may help prevent inappropriate interpolation in areas with rapid change in activation threshold values.

The processor may present, via a display of a computing device, a generated activation area (e.g., an activation volume, an activation contour, or both). In some examples, the processor may include a brain atlas structure or other anatomical atlas in the presentation of the activation area displayed to the user, such that the activation area visually correlates to the anatomy of the patient. The anatomical (e.g., brain) atlas structure may correspond to the area where a stimulation device has been implanted. In some examples in which the anatomical atlas structure is or includes a brain atlas structure, the brain atlas structure may have been modified based on information regarding a patient's actual brain structure. For examples, a brain atlas (brain anatomy) structure may be modified based on information gathered from an image of the patient's brain, such as a magnetic resonance imaging (MRI) image. The area of activation may be presented at any time along the treatment continuum. For example, during preoperative surgical planning, intraoperative targeting, postoperative programming, or troubleshooting of stimulation system.

In some examples, a processor generates graphical representations for a plurality of stimulation parameter sets and stores the graphical representations within a memory. The graphical representations and sets of stimulation parameter values may be associated in the memory, e.g., in a look-up table format. In response to receiving user input selecting (e.g., entering or selecting from a predetermined list) a set of stimulation parameter values, a processor may determine the graphical representation of the activation area associated with the selected set of stimulation parameter values in the memory, and present the graphical representation to a user via the display.

Preloading graphical representations and storing the graphical representations in a memory of a computing device may save computation time for a user. In some examples, the graphical representations for each of a plurality of commonly used stimulation parameter sets (e.g., common to a particular clinician or a plurality of clinicians) are predetermined and stored by the memory. In the event that a graphical representation corresponding to a selected stimulation parameter set has not yet been generated, a processor may generate a new graphical representation based on the selected stimulation parameter set, e.g., using the techniques described herein. In some examples, the processor generates the new graphical representation by interpolation, e.g., linear interpolation, from at least two other graphical representations stored within the memory. The interpolation results in an approximate activation area. The use of interpolation can save computing time and allows for generation of graphical representation by a computing device, such as a simple handheld medical device programmer, that may not have the computing power to generate an activation volume (or other type of activation area) from scratch.

In addition, or instead, of the interpolation, in some examples, the processor may generate the new graphical representation based on a set of neuron representatives and activation thresholds stored in the memory. For example, the processor may generate a new grid including neuronal representatives and respective activation thresholds, and determine whether each of the neuron representatives would be activated in response to delivery of electrical stimulation according to the selected set of stimulation parameter values. In some examples, after generating the new graphical representation, the processor may save the new graphical representation in the memory in order to eliminate the need to regenerate the graphical representation at a later time if the same set of stimulation parameters is selected again.

Predetermining and storing a plurality of graphical representations of activation areas for each of a plurality of sets of stimulation parameter values, e.g., in a look-up table, may help limit the amount of computation done by a programmer (or other computing device) prior to displaying the graphical representation of activation area. The predetermined and stored graphical representations of activation areas may be generated using, for example, multiple computing devices, which may be advantageous if the computing required to generate the graphical representations is relatively complex. For example, electric field calculations, neuron locations, neuron simulations, and other computations needed to provide a graphical representation of the activation area based on a parameter set may be done using multiple computing devices, which may be located remotely relative to the programmer (e.g., cloud computing) or may be located locally relative to the programmer. After the data is determined by the multiple computing devices, the look-up tables with graphical representations of activation areas for different sets of stimulation parameter values, and including the neuron locations and thresholds for a range of different pulse widths and fiber orientations, can be loaded onto the medical device programmer or other computing device. The predetermination and storage of the plurality of graphical representations of activation areas for each of a plurality of sets of stimulation parameter values may enable the programmer to support the generation of a plurality of different graphical representations of activation areas, and give the user the flexibility to select a plurality of different sets of stimulation parameter values, while minimizing the computation time at the point of use by the clinician.

One or more graphical representations of activation areas may provide useful information for a user, e.g., when programming electrical stimulation therapy for a patient. For example, the user may view the one or more graphical representations of activation areas displayed by a computing device, and, based on the displayed graphical representations, the user may determine whether the selected stimulation parameter values would result in the therapy desired (e.g., efficacious therapy). If, for example, the activation area indicated by a graphical representation does not sufficiently cover the desired area, or covers a larger area than desired, the user may modify one or more stimulation parameter values, and, in response to receiving such input, the processor of the computing device may present one or more graphical representations of activation areas that correspond to the modified stimulation parameter values. In some examples, a processor may modify the stimulation parameter values based on user feedback.

In some examples, a processor is configured to display a plurality of graphical representations of activation areas for more than one set of stimulation parameter values at a time. A visual of multiple activation areas at once may allow the user to compare activation areas side by side to better determine which of the sets of stimulation parameter values will provide a relatively more efficacious therapy. In some examples, the multiple activation areas may correspond to multiple possible outcomes for the same therapy parameter set. The different outcomes may correspond to varying fiber orientations at the area of implantation. For example, a processor may present, via a user interface, Grade I, Grade II, and Grade III activation areas, where each of the Grade I, II, and III activation areas may have a different configuration (e.g., size, shape, or both). A Grade I activation area may correspond to a fiber orientation of 90 degrees relative to the longitudinal axis of an implanted lead, and a Grade II activation area may correspond to a fiber orientation of 70 degrees relative to the longitudinal axis of an implanted lead. A Grade III activation area may correspond to a fiber orientation of 50 degrees relative to the longitudinal axis of an implanted lead. The Grade I activation area may correspond to an orientation of neurons resulting in activation thresholds higher than the Grade II and Grade III neurons, and the Grade II activation area may correspond to an orientation of neurons having higher activation thresholds than the Grade III neurons.

In another example, a processor may present, via a user interface, Grade I, Grade II, and Grade III activation areas, where the Grade I activation area may correspond to the activation area in which, for a particular activated neuron representative, all or 100% of fiber orientations associated with the activated neuron representative are activated in response to electrical stimulation delivered via a particular set of stimulation parameter values, the Grade II activation area may correspond to the area in which, for a particular activated neuron representative most, e.g., 80%, of fiber orientations are activated excluding those with the highest thresholds, and the Grade III activation area may correspond to the volume in which, for a particular activated neuron represented within the area of activation, even less, e.g., 60% of fiber orientations associated with the activated neuron representative are activated. In some examples, a user may select the grades or the number of grades to be presented by the processor.

In some examples, the processor, automatically, or based on user input, selects a stimulation parameter set based on the one or more graphical representations of activation areas. The computing device may then transmit the selected stimulation parameter set to a medical device, which may or may not be implanted in the patient. The medical device can then generate and deliver electrical stimulation to the patient based on the selected stimulation parameter set.

FIG. 1 is a conceptual diagram illustrating an example therapy system 10 that is configured to deliver therapy to manage a patient condition, such as a movement disorder, neurodegenerative impairment, a mood disorder or a seizure disorder, of patient 12. Patient 12 ordinarily will be a human patient. In some cases, however, therapy system 10 may be applied to other mammalian or non-mammalian, non-human patients. While movement disorders and neurodegenerative impairment are primarily referred to herein, for purposes of illustration, in other examples, therapy system 10 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post-traumatic stress disorder, dysthymic disorder or obsessive-compulsive disorder (OCD)).

Therapy system 10 includes medical device programmer 14, implantable medical device (IMD) 16, lead extension 18, and leads 20A and 20B with respective sets of electrodes 24, 26. In the example shown in FIG. 1, electrodes 24, 26 of leads 20A, 20B (collectively referred to as "leads 20"), respectively, are positioned to deliver electrical stimulation to a tissue site within brain 28, such as a deep brain site under the dura mater of brain 28 of patient 12. In this example, IMD 16 provides deep brain stimulation (DBS) therapy. In other examples, IMD 16 may provide other therapies, such as, for example, spinal cord stimulation, pelvic floor stimulation, gastric stimulation, occipital nerve stimulation, cardiac stimulation, intrathecal drug delivery, intraparenchymal drug delivery, intracerebroventricular drug delivery, pelvic floor drug delivery, and the like.

In some examples, delivery of stimulation to one or more regions of brain 28, such as the subthalamic nucleus (e.g., the dorsal subthalamic nucleus), globus pallidus, internal capsule, thalamus or motor cortex, may be an effective treatment to mitigate or even eliminate one or more symptoms of movement disorders. A movement disorder or other neurodegenerative impairment may include symptoms such as, for example, muscle control impairment, motion impairment or other movement problems, such as rigidity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

In some examples, electrodes 24, 26 of leads 20 may also be positioned to sense bioelectrical brain signals within brain 28 of patient 12. Electrodes 24 and 26 may each include one or more electrodes. In some examples, some of electrodes 24, 26 may be configured to only sense bioelectrical brain signals and other electrodes 24, 26 may be configured to only deliver electrical stimulation to brain 28. In other examples, some or all of electrodes 24, 26 are configured to both sense bioelectrical brain signals and deliver electrical stimulation to brain 28, e.g., on a selective basis.

IMD 16 includes a therapy module that includes a stimulation generator that is configured to generate and deliver electrical stimulation therapy to patient 12 via a subset of electrodes 24, 26 of leads 20A and 20B, respectively. In some examples, IMD 16 may also be configured to deliver a therapeutic agent (e.g., a drug) to the patient 12. In these cases, leads 20A and 20B may be supplemented or replaced by one or more catheters to deliver the drug. The one or more catheters may carry electrodes such as electrodes 24, 26 used to deliver electrical stimulation therapy to the patient. The subset of electrodes 24, 26 includes at least one electrode and can include a plurality of electrodes. The subset of electrodes 24, 26 that are used to deliver electrical stimulation to patient 12, and, in some cases, the polarity of the subset of electrodes 24, 26, may be referred to as a stimulation electrode combination or configuration. In some examples, the stimulation electrode combination includes a first electrode positioned on a lead 20A or 20B and a reference electrode positioned relatively far from the first electrode (e.g., unipolar stimulation) or two or more electrodes positioned on one or more leads 20A, 20B (e.g., bipolar stimulation or multipolar stimulation).

Electrical stimulation generated by IMD 16 may be configured to manage a variety of disorders and conditions. In some examples, the stimulation generator of IMD 16 is configured to generate and deliver electrical pulses to patient 12 via electrodes of a selected stimulation electrode combination. However, in other examples, the stimulation generator of IMD 16 may be configured to generate and deliver a continuous wave signal, e.g., a sine wave or triangle wave, via the selected electrode combination. In either case, a signal generator within IMD 16 may generate the electrical stimulation therapy for DBS according to a therapy program that is selected at that given time in therapy. In examples in which IMD 16 delivers electrical stimulation in the form of stimulation pulses, a therapy program may include a set of therapy parameter values, such as a stimulation electrode combination for delivering stimulation to patient 12, pulse frequency, pulse charge level, pulse width, and/or a current or voltage amplitude of the pulses. As previously indicated, the stimulation electrode combination may indicate the specific electrodes 24, 26 that are selected to deliver stimulation signals to tissue of patient 12 and the respective polarity of the selected electrodes.

The locations of leads 20 can be determined using any suitable technique, such as based on a medical image generated using any suitable imaging modality (e.g., computed tomography (CT), magnetic resonance imaging (MRI), x-ray or fluoroscopy), based on the stereotactic coordinates used to implant leads 20 within brain 28, based on correlations of signals sensed by IMD 16 with anatomical structures expected to yield those signals, correlations of stimulation effects at electrodes with anatomical structures expected to yield those effects, or based on a clinician-estimated location of leads 20 within brain 28.

After selecting stimulation electrode combinations, a clinician, alone or with the aid of a computing device, such as programmer 14, may select the other stimulation parameter values that provide efficacious therapy to patient 12. These other stimulation parameter values may include, for example, an amplitude of stimulation signals, a pulse width, and, in the case of stimulation pulses, a pulse rate (i.e., pulse frequency) and/or a duty cycle of the stimulation signals, and an electrode configuration (e.g., selected combination and polarities) of electrodes. In other cases, programmer 14 may suggest information about the stimulation waveform as well as pattern of delivered stimulation pulses.

In some examples, programmer 14 or another computing device is configured to present a visual display of a graphical representation of the area of tissue activated by electrical stimulation delivered according to a set of stimulation parameter values. The display may help a user or programmer 14 select one or more sets of stimulation parameter values that may result in efficacious electrical stimulation therapy to patient 12. While programmer 14 is primarily referred to herein as the computing device that is configured to display the one or more graphical representations representing the area of tissue activated by electrical stimulation, in other examples, another computing device may perform any of the techniques described herein with reference to programmer 14. For example, a remote computer connected to a local display (local to the clinician) may present, via the local display, the one or more graphical representations of the area of tissue activated by electrical stimulation in accordance with the examples described herein.

The graphical representation of the activation area may be, for example, a simulation of neuron activation area in response to electrical stimulation provided by a set of stimulation parameter values (e.g., pulse width, amplitude, and electrode combination). A user may select the stimulation parameter values that result in the desired stimulation area based on the graphical representations presented by the programmer 14. The selected stimulation parameter values may then be provided to IMD 16, which may deliver electrical stimulation therapy to patient 12 in accordance with the selected stimulation parameter values. In some examples, the user may provide input to programmer 14 that indicates the criteria for the electrical stimulation. For example, the user may provide input to select an area in the body of patient 12 to be covered by the activation area or to be avoided (e.g., inactivated by the electrical stimulation). Programmer 14 may suggest one or more stimulation parameter sets that result in an activation area that fits within the criteria selected by the user. The user may then select the desired stimulation parameters for programming to be provided to the IMD 16 from the suggested stimulation parameter sets.

In some examples, after IMD 16 is implanted within patient 12 and programmed for chronic therapy delivery, programmer 14, IMD 16, or another device may periodically reassess the selected stimulation electrode combination to determine whether another stimulation electrode combination, or other stimulation parameter values, may provide more efficacious therapy. IMD 16 may determine, for example, whether the target tissue site for stimulation therapy has changed based on physiological changes in brain 28, whether one or both leads 20A, 20B have migrated away from the original implant site within brain 28, or whether the leads have migrated relative to one another.

IMD 16 may be implanted within a subcutaneous pocket above the clavicle, or, alternatively, the abdomen, back or buttocks of patient 12, on or within cranium 32 or at any other suitable site within patient 12. Generally, IMD 16 is constructed of a biocompatible material that resists corrosion and degradation from bodily fluids. IMD 16 may comprise a hermetic housing to substantially enclose components, such as a processor, therapy module, and memory.

As shown in FIG. 1, implanted lead extension 18 is coupled to IMD 16 via connector 30 (also referred to as a connector block or a header of IMD 16). In the example of FIG. 1, lead extension 18 traverses from the implant site of IMD 16 and along the neck of patient 12 to cranium 32 of patient 12 to access brain 28. In the example shown in FIG. 1, leads 20 are implanted within the right and left hemispheres, respectively, of patient 12 in order to deliver electrical stimulation to one or more regions of brain 28, which may be selected based on the patient condition or disorder controlled by therapy system 10. The stimulation electrodes used to deliver stimulation to the target tissue site may be selected based on one or more graphical representations of activation areas of corresponding to one or more sets of stimulation parameter values. Other lead 20 and IMD 16 implant sites are contemplated. For example, IMD 16 may be implanted on or within cranium 32, in some examples. As another example, leads 20 may be implanted within the same hemisphere of brain 28 or IMD 16 may be coupled to a single lead. In other examples, IMD 16 may be coupled to a leadless stimulator.

Although leads 20 are shown in FIG. 1 as being coupled to a common lead extension 18, in other examples, leads 20 may be coupled to IMD 16 via separate lead extensions or directly to connector 30. Leads 20 may be positioned to deliver electrical stimulation to one or more target tissue sites (also referred to herein as "therapy targets") within brain 28 to manage patient symptoms associated with a patient condition, such as a movement disorder. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. For example, electrodes 24, 26 may be surgically implanted under or over the dura mater of brain 28 or within the cerebral cortex of brain 28 via a burr hole in cranium 32 of patient 12, and electrically coupled to IMD 16 via one or more leads 20.

In the example shown in FIG. 1, electrodes 24, 26 of leads 20 are shown as ring electrodes. Ring electrodes may be used in DBS applications because they are relatively simple to program and are capable of delivering an electrical field to any tissue adjacent to electrodes 24, 26. In other examples, electrodes 24, 26 may have different configurations. For example, in some examples, at least some of the electrodes 24, 26 of leads 20 may have a complex electrode array geometry that is capable of producing shaped electrical fields. The complex electrode array geometry may include multiple electrodes (e.g., partial ring or segmented electrodes) around the outer perimeter of each lead 20, rather than one ring electrode. In this manner, electrical stimulation may be directed in a specific direction from leads 20 to enhance therapy efficacy and reduce possible adverse side effects from stimulating a large volume of tissue.

In the example shown in FIG. 1, IMD 16 includes a memory (shown in FIG. 2) that stores a plurality of therapy programs that each define a set of therapy parameter values. In some examples, IMD 16 may select a therapy program from the memory based on various parameters, such as a detected patient activity level, a detected patient state, based on the time of day, and the like. IMD 16 may generate electrical stimulation based on the selected therapy program to manage the patient symptoms associated with a movement disorder (or another patient condition). In accordance with the techniques of this disclosure, in some examples, the memory of IMD 16 may store graphics processing data, including a non-uniform grid of neuron representatives and activation threshold values at the grid locations that may be applied during a rendering process to produce a graphical representation of the area of activation. A computing device, such as programmer 14, may retrieve the graphical processing data, e.g., via wireless telemetry, to perform the rendering process using the graphical processing data. In other examples, programmer 14 or another device (e.g., a device remote from programmer 14 and communicatively coupled to programmer 14) stores the graphics processing data.

External programmer 14 wirelessly communicates with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 16. Moreover, a clinician programmer may be configured to perform a rendering process using the graphics processing data stored on IMD 16, whereas a patient programmer is typically not (though may be) configured to perform the rendering process. The programmer may also communicate with an external trial stimulator device if IMD 16 is not implanted in patient 12 in order to do preliminary testing of stimulation parameters prior to device implantation.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate through the user interface of programmer 14 and provide input. If programmer 14 includes buttons and a keypad, the buttons may be dedicated to performing a certain function, i.e., activation of power, or the buttons and the keypad may be soft keys that change in function depending upon the section of the user interface currently viewed by the user. Alternatively, the screen (not shown) of programmer 14 may be a touchscreen that allows the user to provide input directly to the user interface shown on the display. The user may use a stylus or a finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as medical device programmer 14. A wireless adapter coupled to the computing device may enable secure communication between the computing device and IMD 16. Elements of programmer 14 may also be implemented using networked computing resources such that some computation (e.g., of activation areas) can occur remotely.

When programmer 14 is configured for use by the clinician, programmer 14 may be used to transmit initial programming information to IMD 16. This initial information may include hardware information, such as the type of leads 20 and the electrode arrangement, the position of leads 20 within brain 28, the configuration of electrode array 24, 26, initial programs defining therapy parameter values, and any other information the clinician desires to program into IMD 16. Programmer 14 may also be capable of completing functional tests (e.g., measuring the impedance of electrodes 24, 26 of leads 20).

The clinician may also store therapy programs within IMD 16 with the aid of programmer 14. During a programming session, the clinician may determine one or more therapy programs that provide efficacious therapy to patient 12 to address symptoms associated with the patient condition. For example, the clinician may select one or more stimulation electrode combinations with which stimulation is delivered to brain 28. During the programming session, patient 12 may provide feedback to the clinician as to the efficacy of the specific program being evaluated or the clinician may evaluate the efficacy based on one or more physiological parameters of patient 12 (e.g., muscle activity or muscle tone). Programmer 14 may assist the clinician in the creation/identification of therapy programs by providing a methodical system for identifying potentially beneficial therapy parameter values. For example, a clinician may make an initial selection of a set of therapy parameter values. A graphical representation of an area of activation resulting from the set of therapy parameter values. The clinician may adjust the set of therapy parameter values based on the graphical representation displayed.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Programmer 14 may also provide an indication to patient 12 when therapy is being delivered, when patient input has triggered a change in therapy or when the power source within programmer 14 or IMD 16 needs to be replaced or recharged. For example, programmer 14 may include an alert LED, may flash a message to patient 12 via a programmer display, generate an audible sound or somatosensory cue to confirm patient input was received, e.g., to indicate a patient state or to manually modify a therapy parameter.

Programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the IEEE 802.11 or Bluetooth® specification sets, infrared (IR) communication according to the IRDA specification set, or other standard or proprietary telemetry protocols. Programmer 14 may also communicate with other programming or computing devices via exchange of removable media, such as magnetic or optical disks, or memory cards. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 can be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads, implanted leads via a percutaneous extension or one or more external leads. If the trial stimulator indicates DBS system 10 provides effective treatment to patient 12, the clinician may implant a chronic stimulator within patient 12 for relatively long-term treatment.

In other examples of therapy system 10, therapy system 10 includes only one lead or more than two leads. The devices, systems, and techniques described below can be applied to a therapy system that includes only one lead or more than two leads.

In still other examples, therapy system 10 may comprise a leadless IMD that carries one or more electrodes on the housing of the device. The IMD may by a relatively small microstimulator system that allows implantation of the device at a location that will receive stimulation. In this case, the therapy delivery element may comprise the IMD but does not comprise any other leads or catheters.

Figure 2:
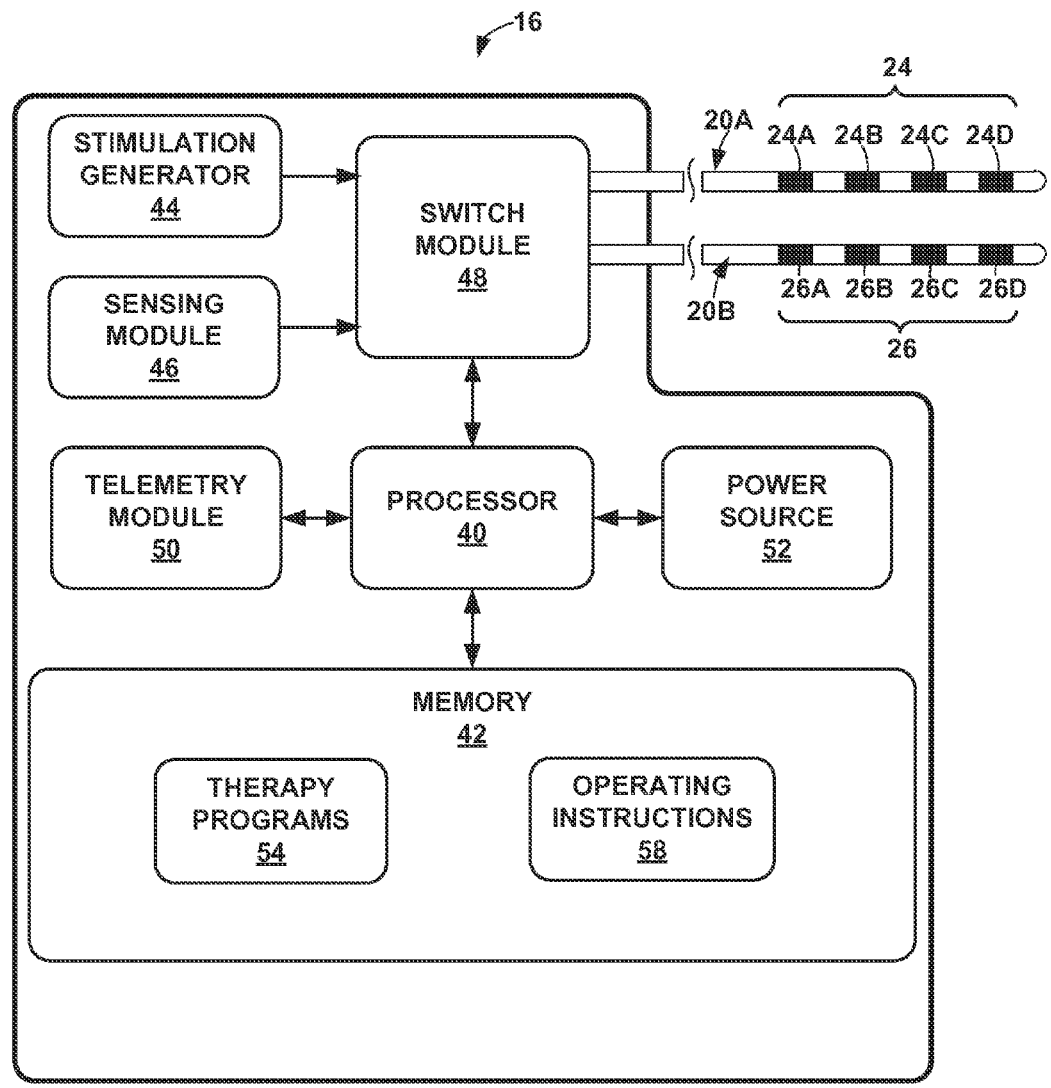
FIG. 2 is a functional block diagram illustrating components of an example implantable medical device (IMD).

FIG. 2 is a functional block diagram illustrating components of an example IMD 16. In the example shown in FIG. 2, IMD 16 includes processor 40, memory 42, electrical stimulation generator 44, sensing module 46, switch module 48, telemetry module 50, and power source 52. Memory 42 may include any volatile or non-volatile media, such as a random access memory (RAM), read only memory (ROM), non-volatile RAM (NVRAM), electrically erasable programmable ROM (EEPROM), flash memory, and the like. Memory 42 may store computer-readable instructions that, when executed by processor 40, cause IMD 16 to perform various functions, such as those described herein.

In the example shown in FIG. 2, memory 42 stores therapy programs 54, and operating instructions 58, within memory 42 or separate areas within memory 42. In some examples, memory 42 represents separate memories for individually storing therapy programs 54, and operating instructions 58. Each stored therapy program 54 defines a particular set of electrical stimulation parameters, such as a stimulation electrode combination, current or voltage amplitude, frequency (e.g., pulse rate in the case of stimulation pulses), and pulse width. Operating instructions 58 guide general operation of IMD 16 under control of processor 40.

Processor 40 may include any combination of one or more of a microprocessor, a controller, a digital signal processor (DSP), an application specific integrated circuit (ASIC), a field-programmable gate array (FPGA), or discrete logic circuitry. The functions attributed to processors described herein may be embodied in a hardware device via software, firmware, hardware or any combination thereof. Processor 40 is configured to control stimulation generator 44 according to therapy programs 54 stored in memory 42 to apply particular stimulation parameter values specified by one or more of programs, such as amplitude, pulse width, and pulse rate. Processor 40 may control stimulation generator 44, sensing module 46, and switch module 48, among other elements of IMD 16, to deliver therapy to patient 12 via selected electrodes 24, 26 carried by leads 20, according to specified stimulation parameters. Accordingly, portions of IMD 16, e.g., processor 40, stimulation generator 44, sensing module 46, and switch module 48, may collectively be referred to as a therapy module of IMD 16.

In the example shown in FIG. 2, the set of electrodes 24 includes electrodes 24A, 24B, 24C, and 24D, and the set of electrodes 26 includes electrodes 26A, 26B, 26C, and 26D. In the example shown in FIG. 2, processor 40 is configured to control switch module 48 to apply the stimulation signals generated by stimulation generator 44 to selected combinations of electrodes 24, 26. In particular, switch module 48 may couple stimulation signals to selected conductors within leads 20, which, in turn, deliver the stimulation signals across selected electrodes 24, 26. Switch module 48 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 44 is coupled to electrodes 24, 26 via switch module 48 and conductors within leads 20. In some examples, however, IMD 16 does not include switch module 48 and instead contains a separate stimulation generator for each electrode.

Stimulation generator 44 can be a single channel or multi-channel stimulation generator. In particular, stimulation generator 44 may be capable of delivering a single stimulation pulse, multiple stimulation pulses, or a continuous signal at a given time via a single electrode combination or multiple stimulation pulses at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12.

Sensing module 46, under the control of processor 40, may sense bioelectrical brain signals and provide the sensed bioelectrical brain signals to processor 40. Processor 40 may control switch module 48 to couple sensing module 46 to a selected combinations of electrodes 24, 26, e.g., a sense electrode combination. In this way, IMD 16 is configured such that sensing module 46 may sense bioelectrical brain signals with a plurality of different sense electrode combinations. Switch module 48 may be electrically coupled to the selected electrodes 24, 26 via the conductors within the respective leads 20, which, in turn, deliver the bioelectrical brain signal sensed across the selected electrodes 24, 26 to sensing module 46. The bioelectrical brain signal may include electrical signals that are indicative of electrical activity within brain 28 of patient 12. Processor 40 can store the sensed bioelectrical brain signals in memory 42.

Although sensing module 46 is incorporated into a common housing with stimulation generator 44 and processor 40 in FIG. 2, in other examples, sensing module 46 may be in a separate housing from IMD 16 and may communicate with processor 40 (and, in some examples, programmer 14) via wired or wireless communication techniques.

Telemetry module 50 supports wireless communication between IMD 16 and an external programmer 14 or another computing device under the control of processor 40. Processor 40 of IMD 16 may receive, as updates to therapy programs, values for various stimulation parameters such as amplitude and electrode combination, from programmer 14 via telemetry module 50. The updates to the therapy programs may be stored within therapy programs 54 portion of memory 42. Telemetry module 50 in IMD 16, as well as telemetry modules in other devices and systems described herein, such as programmer 14, may accomplish communication by RF communication techniques. In addition, telemetry module 50 may communicate with external medical device programmer 14 via proximal inductive interaction of IMD 16 with programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
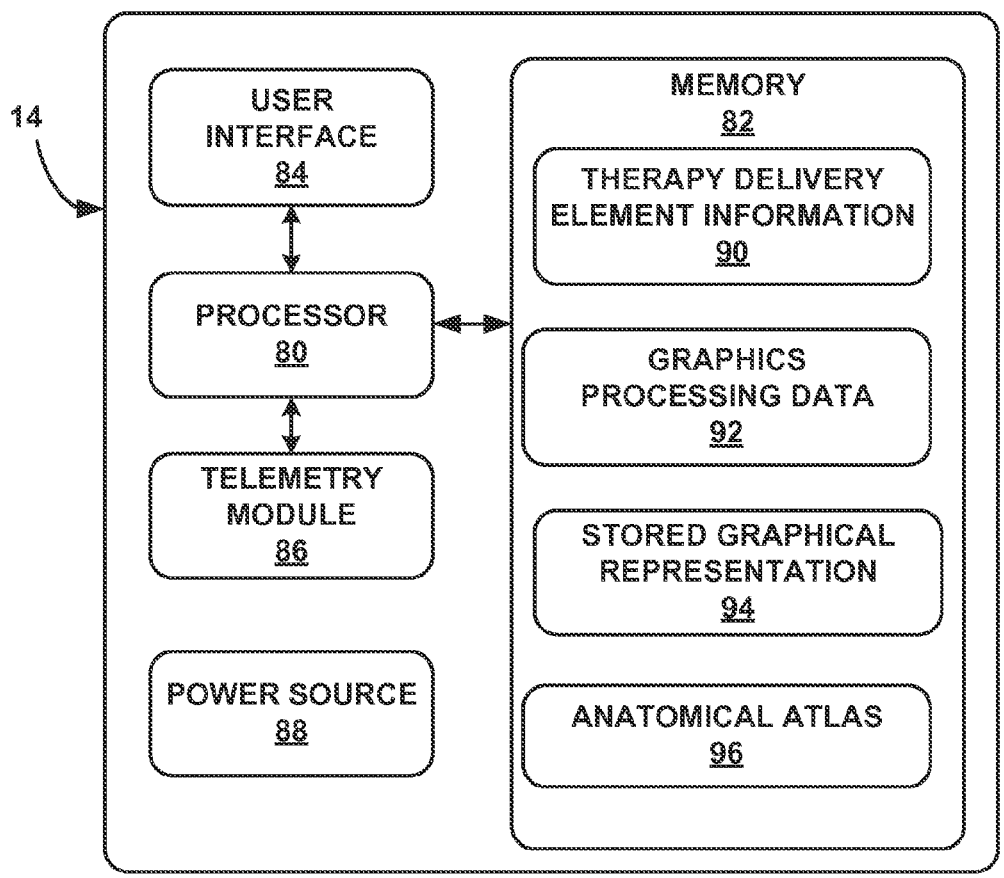
FIG. 3 is a functional block diagram illustrating components of an example external medical device programmer.

FIG. 3 is a conceptual block diagram of an example external medical device programmer 14, which includes processor 80, memory 82, user interface 84, telemetry module 86, and power source 88. Processor 80 is configured to control user interface 84 and telemetry module 86, and store and retrieve information and instructions to and from memory 82. Programmer 14 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80.

A user, such as a clinician or patient 12, may interact with programmer 14 through user interface 84. Example techniques of this disclosure are directed to generating and storing graphical model representations of an area (e.g., a volume) of tissue activated during deep brain stimulation or other electrical stimulation therapy. The information may be used to determine efficacious stimulation parameter values for provide therapy to patient 12. In some examples, stimulation parameter values chosen based on the graphical model representations may be transmitted to IMD 16 at a time different from when rendering of the graphical representations occurs. Accordingly, when programmer 14 is configured as a patient programmer, in some examples, the patient programmer is not necessarily configured to perform the rendering process using graphics processing data 92 and processor 80.

In some examples, when programmer 14 is configured as a clinician programmer, processor 80 may be configured to perform the rendering process using graphics processing data 92 to generate a graphical representation of an area of activation. In some example, processor 80 may be configured to render a graphical representation of an area of activation superimposed over an anatomical feature including the therapy target of patient 12, and to display the graphical representation, e.g., via user interface 84. The anatomical feature may be an anatomical image of the target tissue site of patient 12, a reference anatomical image, which may not be specific to patient 12, or an anatomical atlas indicating specific structures of the patient's anatomy.

User interface 84 includes a display (not shown), such as a LCD or LED display or other type of screen, to present information related to the therapy, such as information related to current stimulation parameter values (including electrode combinations) and in some examples, when configured to render graphics objects, a graphical representation of an area of activation and an anatomical feature including a therapy target of patient 12. In addition, user interface 84 may include an input mechanism configured to receive input from the user. The input mechanisms may include, for example, buttons, a keypad (e.g., an alphanumeric keypad), a peripheral pointing device, or another input mechanism that allows the user to navigate through user interfaces presented by processor 80 of programmer 14 and provide input. The input may include, for example, changes to current or proposed stimulation parameter values (e.g., one or more of a pulse width value, an amplitude value, or a selection of electrode combinations).

In examples in which programmer 14 includes buttons and a keypad, the buttons may be dedicated to performing a certain function, e.g., a power button, or the buttons and the keypad may be soft keys that change in function depending upon the section of the user interface currently viewed by the user. In addition, or instead of buttons, a keypad, or both, the display (not shown) of programmer 14 may be a touch screen that allows the user to provide input directly to the user interface shown on the display. The user may use a stylus or a finger to provide input to the display. In other examples, user interface 84 also includes audio circuitry for providing audible instructions or sounds to patient 12 and/or receiving voice commands from patient 12, which may be useful if patient 12 has limited motor functions. Patient 12, a clinician or another user may also interact with programmer 14 to manually select therapy programs, generate new therapy programs, modify therapy programs through individual or global adjustments, and transmit the new programs to IMD 16.

In some examples, at least some of the control of therapy delivery by IMD 16 may be implemented by processor 80 of programmer 14. A clinician or other user may interact with the programmer 14 to determine the efficacy of one or more proposed stimulation parameter sets via model graphical representations of an area of activation provided by the proposed stimulation parameter values.

In the example shown in FIG. 3, memory 82 stores therapy delivery element information 90, graphics processing data 92, graphical representations of activation areas 94, and anatomical atlas 96 in separate memories within memory 82 or separate areas within memory 82. Memory 82 may also include instructions for operating user interface 84 and telemetry module 86, and for managing power source 88. Memory 82 may also store any therapy data retrieved from IMD 16 during the course of therapy, such as bioelectrical brain signals sensed by IMD 16. The clinician may use this therapy data to determine the progression of the patient condition in order to predict future treatment. Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Therapy delivery element information 90 includes one or more graphical representations and data regarding at least one therapy delivery element. In some examples, the therapy delivery element may be a lead. In some examples the therapy delivery element may be a leadless stimulator. In some examples, therapy delivery element information 90 includes a graphical representation of the portion of a lead implanted within patient 12 including a representation of the electrode type, size and spacing included on the lead. Therapy delivery element information may also store information regarding the electrode type, size and spacing for use by processor 80 in one or more algorithms implemented to produce a graphical representation of an expected activation area. In some examples, therapy delivery element information 90 may store information corresponding to a plurality of therapy delivery element types. For example, information may be stored corresponding to one or more leadless stimulators and a plurality of lead types. A user, through user interface 84, may select a lead type that corresponds to the lead type implanted in patient 12. In some examples a user may select two lead representations for display, such as a lead representation corresponding to lead 20A and a lead representation corresponding to lead 20B. In some examples, therapy delivery element information 90 may store information regarding spacing between two more leads when implanted. In response to a selection by the user, the stored graphical representation of the lead is displayed on a display that is a part of user interface 84. Information regarding the relative spacing of the electrode on the chosen lead is provided to processor 80. In instances in which two or more leads have been selected for display, a user may provide information regarding the relative locations of the two or more leads. In some examples, a user may select from common configurations stored within therapy delivery element information 90.

Graphics processing data 92 stores information with which processor 80 of programmer 14 may, when configured to perform a rendering process, render a graphical representation of an area of activation surrounding the lead chosen from therapy delivery element information 90. Graphics processing data 92 may include instructions defining an algorithm, explained in more detail below, by which processor 80 generates a 2D or 3D image of an activation area for a selected lead and a set of stimulation parameter values. In some examples, based on instructions from graphics processing data 92, processor 80 accesses information in therapy delivery element information 90 regarding the spacing between two electrodes selected by a user.

In examples in which processor 80 generates a graphical representation of an activation area based on a non-uniform grid of neuron representatives, in addition to generating the graphical representation based on therapy delivery element information 90, processor 80 may generate the graphical representation based on information stored in anatomical atlas 96 regarding the activation threshold. For example, anatomical atlas 96 may include information regarding a particular neuron type and the amplitude (current or voltage) and pulse width combination that is needed to generate a propagating action potential along the neuron, where the amplitude may be the activation threshold value. By using information from the anatomical atlas 96 in addition to the area of activation based on a non-uniform grid of neuron representatives, programmer 14 may provide a more accurate visualization of the area of tissue that would be activated by a particular set of stimulation parameter values.

In response to receiving a set of stimulation parameter values, processor 80 may determine if a graphical representation of an activation area has previously been generated using the same stimulation parameter values and therapy delivery element selection. For example, processor 80 may determine whether a graphical representation of an activation area has been generated for the particular combination of pulse width, amplitude, and electrode combination defined by the set of stimulation parameter values. Stored graphical representations 94 may store activation areas previously generated for one or more sets of stimulation parameter values. Stored graphical representations 94 may store activations contours, activation volumes or both for each set of stimulation parameters. In some examples, stored graphical representations 94 includes the data needed for processor 80 to recreate the graphical representation, such as a grid of neuron representatives used to generate the graphical representation and an array of thresholds at each point on the grid.

If processor 80 determines that a graphical representation is stored in stored graphical representation 94 that corresponds to the selected set of stimulation parameter values, then processor 80 may retrieve the stored graphical representation from stored graphical representations 94 and display the graphical representation via a display of user interface 84. If no corresponding graphical representation is stored in stored graphical representations 94, then processor 80 may generate a graphical representation of an area of activated by the selected set of stimulation parameter values, either in its entirety or by interpolating the graphical representation from other graphical representations.

As explained in more detail below with respect to FIGS. 5-9, in some examples, processor 80, or another processor, generates a graphical representation of an activation area associated with a particular set of stimulation parameter values by determining an electric field resulting from the electrode combination of the set of stimulation parameter values. For single cathode or double cathode unipolar stimulation, a voltage of 1 volt (V) may be applied by setting a boundary to 1V and the selected (active) electrode(s) to 0V. For other configurations 1V may be assigned to the anode(s) and 0V to the cathode(s). The potential distribution is modeled as though generated in a homogenous tissue medium, and is calculated from the Laplace equation $\nabla \cdot \sigma \nabla V = 0$, where V refers to the extracellular potential and a refers to the electrical conductivity of the medium. The result of the calculation may be referred to as a stimulation field solution, i.e., the distribution of voltages within the surrounding medium.

In this example of generating the graphical representation of an activation area, after determining the electric field, processor 80 generates a uniform neuron representative grid, which includes a plurality of substantially evenly (e.g., evenly space or nearly evenly) spaced neuron representative indicating neuron locations. In some examples, the fiber of each neuron representative is oriented substantially perpendicular to the longitudinal axis of the lead including the electrodes of the set of stimulation parameter values being evaluated. In some examples, the neuron representatives may be spaced between about 0.1 mm and about 0.5 mm apart, such as about 0.25 mm apart. In other examples, processor 80 generates, a non-uniform neuron representative grid, in which the neuron representatives are not evenly space. Instead, the non-uniform grid may include two or more different spacings for neuron representatives, where the spacing between adjacent neuron representatives may be based on predicted areas where more or less detail will be needed. In some examples, neuron representatives are spaced about 0.25 mm to about 1 mm apart in the non-uniform grid.

Processor 80 may determine an activation threshold for each neuron representative of the grid (uniform or non-uniform). As discussed above, the activation threshold is the voltage or current that would generate a propagating action potential along the axon represented by the neuron representative. In some examples, the activation threshold is determined using a neuron simulator. As discussed below with respect to FIG. 8, for example, the neuron simulator may apply an electric field solution, and apply increasing amplitudes at a particular pulse width to a neuron representative until the neuron representative is activated. In examples in which processor 80 generates a non-uniform grid, processor 80 may start with a uniform grid and add additional neuron representatives to the grid, based on the activation thresholds of adjacent neuron representatives. For example, processor 80 can cycle through pairs of adjacent neuron representatives to add additional grid points (additional neuron representatives) when the neuron representative pair meets certain criteria. The steps are repeated until the grid points no longer meet the criteria indicating additional grid points should be added. The criteria may indicate, for example, a relatively large difference between the activation thresholds of the adjacent neuron representatives, which may indicate a greater resolution of neuron representatives may be useful for more accurately visualizing the activation area.

In some examples, processor 80 adds an additional neuron representative between a pair of adjacent neuron representatives in response to determining one of the neuron representatives of the pair has a threshold below a selected maximum stimulation amplitude and the difference between the thresholds of the two neuron representatives of the pair is greater than twice the selected maximum stimulation amplitude. In this example, processor 80 adds the additional neuron representative in the middle of the pair of neuron representatives.

Processor 80 may evaluate neuron representative pairs in two dimensions if the initial starting grid is 2D. For example, if considering a neuron grid in the Y-Z plane, processor 80 may scan through adjacent neuron representatives in the Y-axis direction, thereby scanning each pair of adjacent neuron representatives in a column. The scan may be in the backwards and forwards directions (high to low values of Z in the z-axis direction but also low to high values of Z locations for each column). If the criteria for adding a neuron representative are met, then processor 80 can add a neuron representative at that particular Z-axis location (also referred to as a particular value of Z) at a midway point between the neuron representatives of the pair meeting the criteria in the column extending in the Y-axis direction. In some cases, processor 80 adds a set of new neuron representatives at the identified Z-axis location for all values of Y (all columns of the grid).

Similarly, once processor 80 completes the scan of neuron representative pairs (adjacent neuron representatives) extending in the Y-axis direction, processor 80 can scan neuron representative pairs in the Z-axis direction for all rows of grid points. Adjacent neuron representatives may be scanned for meeting the criteria in the backwards and forward directions (high to low values of Y in the y-axis direction and low to high values of Y locations in each row). If the criteria for adding a neuron representative are met, then processor 80 can add a neuron representative at that particular Y-axis location midway between the neuron representatives of the pair meeting the criteria. In some cases, a set of neuron representatives may be added at the identified Y-axis location for all Z values (all rows of the grid).

Anatomical atlas 96 may include graphical representations of various anatomical structures of patient 12, e.g., various anatomical structures of the brain of patient 12. In some examples, the structures may be model structures not specific to patient 12. In other examples, the anatomical structures may be modified to a patient specific model based on information from a medical image of patient 12, such as, for example, a magnetic resonance image (MRI). In some examples, data with which processor 80 can generate a graphical representation of various anatomical structures is stored in anatomical atlas 96. Processor 80 may retrieve, from memory 82, a graphical representation of a location selected by a user. In some examples, the location may be where the lead is implanted in patient 12. In some examples, processor 80 overlays (e.g., merges) a graphical representation of the area of activation with the graphical representation of one or more anatomical structures of patient 12 and presents the merged information via a display of user interface 84.

Anatomical atlas 96 may also store information regarding various neuron characteristics. For example, anatomical atlas 96 may store information regarding the voltage needed to generate a propagating action potential within a particular neuron type or area of the brain.

Power source 88 delivers operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate. Power source 88 may include circuitry to monitor power remaining within a battery. In this manner, user interface 84 may provide a current battery level indicator or low battery level indicator when the battery needs to be replaced or recharged. In some cases, power source 88 may be capable of estimating the remaining time of operation using the current battery.

Figure 4A:
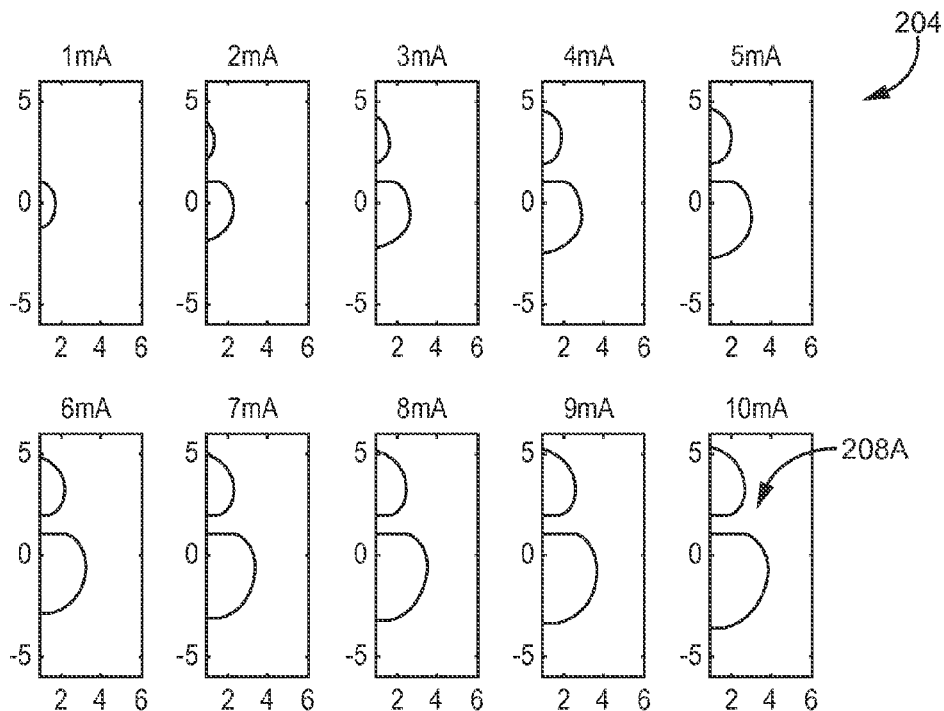
FIG. 4A is a conceptual diagram illustrating an example graphical user interface displaying example activation contours based on a uniform grid of neuron representatives.
Figure 4B:
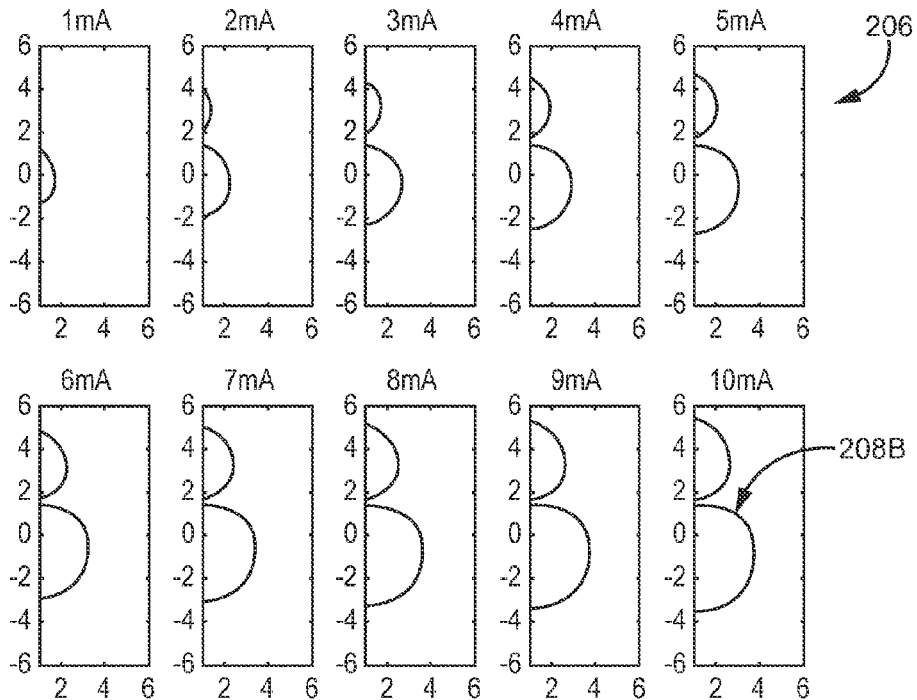
FIG. 4B is a conceptual diagram illustrating an example graphical user interface displaying example activation contours based on a non-uniform grid of neuron representatives.

FIGS. 4A and 4B illustrate a comparison between a uniform grid of neuron representatives, and a non-uniform grid of neuron representatives. Graphical representation 204 (FIG. 4A) includes a number of 2D images of activation contours at varying stimulation amplitudes created using a grid with uniform spacing between the neuron representatives. The neuron representatives in the grid used to create the activation contours of graphical representation 204 are spaced approximately 0.5 mm apart.

Graphical representation 206 (FIG. 4B) includes a number of 2D images of activation contours at the same amplitudes shown in graphical representation 204 made with a non-uniform grid of neuron representatives. A portion of the neuron representatives in the activation contours of graphical representation 206 are approximately 0.5 mm apart, similar to those in graphical representation 204. However, a portion of the neuron representatives in graphical representation 206 are closer together, with a spacing of approximately 0.25 mm or approximately 0.125 mm. The portion with the closer spacing is determined, e.g., by processor 80 of programmer 14 or a processor of another computing device, based checking thresholds of adjacent neuron representative pairs with an algorithm, as discussed in more detail below with respect to FIG. 5.

One difference in results between the generation of activation contours using a uniform grid and a non-uniform grid is illustrated by spaces 208A and 208B. Both are part of an activation contour resulting from electrical stimulation provided at an amplitude of 5 mA. However, the activation contours around space 208A cut off dramatically, while the activation contours around 208B slope, creating a much smaller space with no activation. The activation contours of 208B more accurately represent the area of activation resulting from the selected set of stimulation parameter values.

Figure 4C:
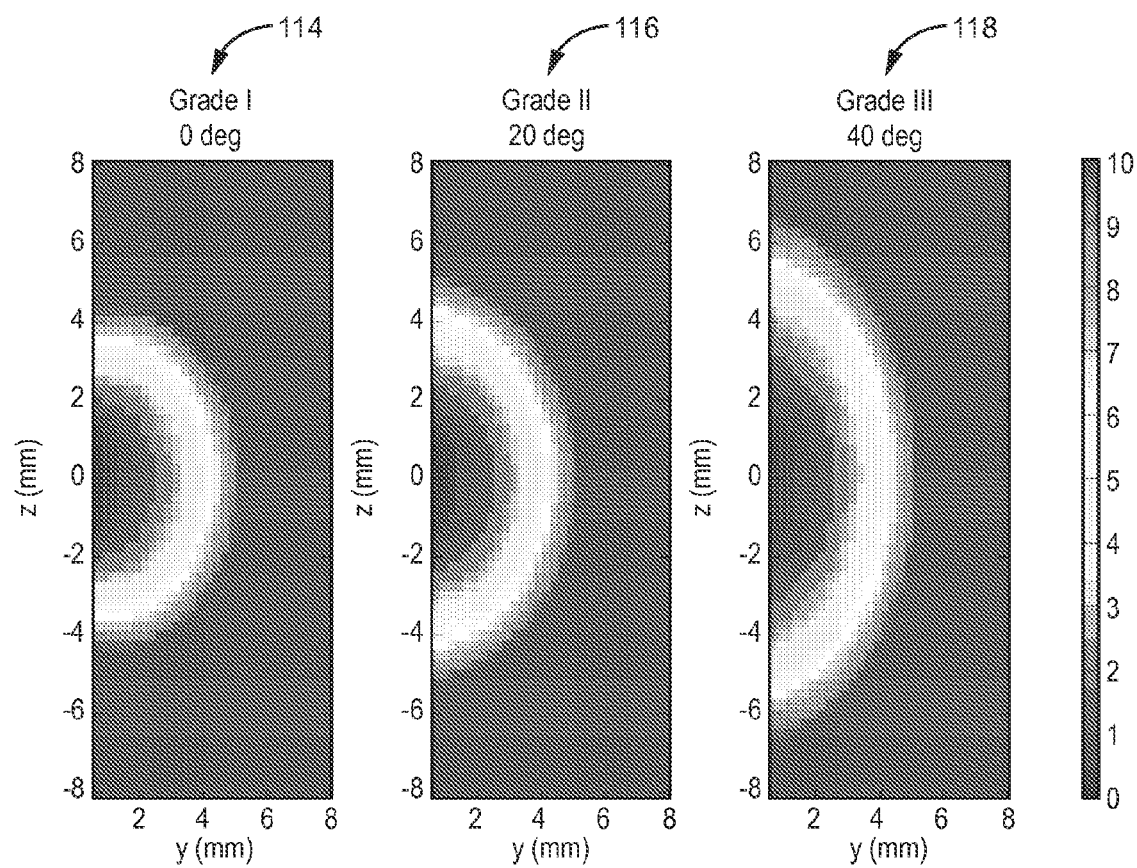
FIG. 4C is a conceptual diagram illustrating an example graphical user interface displaying example activation contours for a plurality of probability groupings.

FIG. 4C is a conceptual diagram illustrating an example graphical user interface (GUI) displaying example activation contours for a plurality of fiber orientations. The GUI may be, for example, generated by processor 80 and presented on a display of user interface 84 of programmer 14 (FIG. 3). As shown in FIG. 4C, a set of stimulation parameter values may result in different areas of activation depending on the orientation of the fibers relative to the lead and electrodes. Thus, it may be useful for the user to view the activation area for a plurality of fiber orientations in order get a more complete picture of the activation area that may result from a particular set of stimulation parameter values.

As shown in FIG. 4C, the GUI includes three activation areas during single cathode monopolar stimulation corresponding to neuron representative fiber orientations of 0 degrees (114), 20 degrees (116), and 40 degrees (118) relative to the axial plane orthogonal to the lead (e.g., 0 degrees are fibers oriented perpendicular to the lead). As discussed through the application, the longitudinal axis of the lead representative is aligned with the Z-axis. Activation area 114 corresponding to the 0 degree fiber orientation (perpendicular to the lead representative) shows an area of tissue activation corresponding to an area most likely to be activated by the application of stimulation based on a selected set of stimulation parameter values. If activation area 114 covers more than the desired activation area, then the set of stimulation parameters values will generate an electrical stimulation field that covers more than the desired activation area.

Depending on the orientation of axons in the location of implantation, the activation area may or may not cover the desired activation area. Activation areas 116 and 118 provide possible activation areas that may result from the same set of stimulation parameter values as those used to simulate activation area 114. Activation area 116 corresponding to the 20 degree orientation includes the additional activation area because there are more neuron representatives with lower activation thresholds when rotated 20 degrees around the Y-axis. Activation area 118 corresponding to the 40 degree orientation includes the activation of additional neuron representatives over the activation area corresponding to 0 degree orientation and 20 degree orientation.

Together, activation areas 114, 116, 118 may represent a range (or at least a partial range) of the activation areas that may result from delivery of electrical stimulation according to a common set of stimulation parameter values. Processor 80 may present the three different activation areas 114, 116, 118 via user interface 84, and a user may view the activation areas 114, 116, 118 in order to select one or more sets of stimulation parameter values based on a plurality of tissue activation areas corresponding to respective fiber angles.

Figure 5:
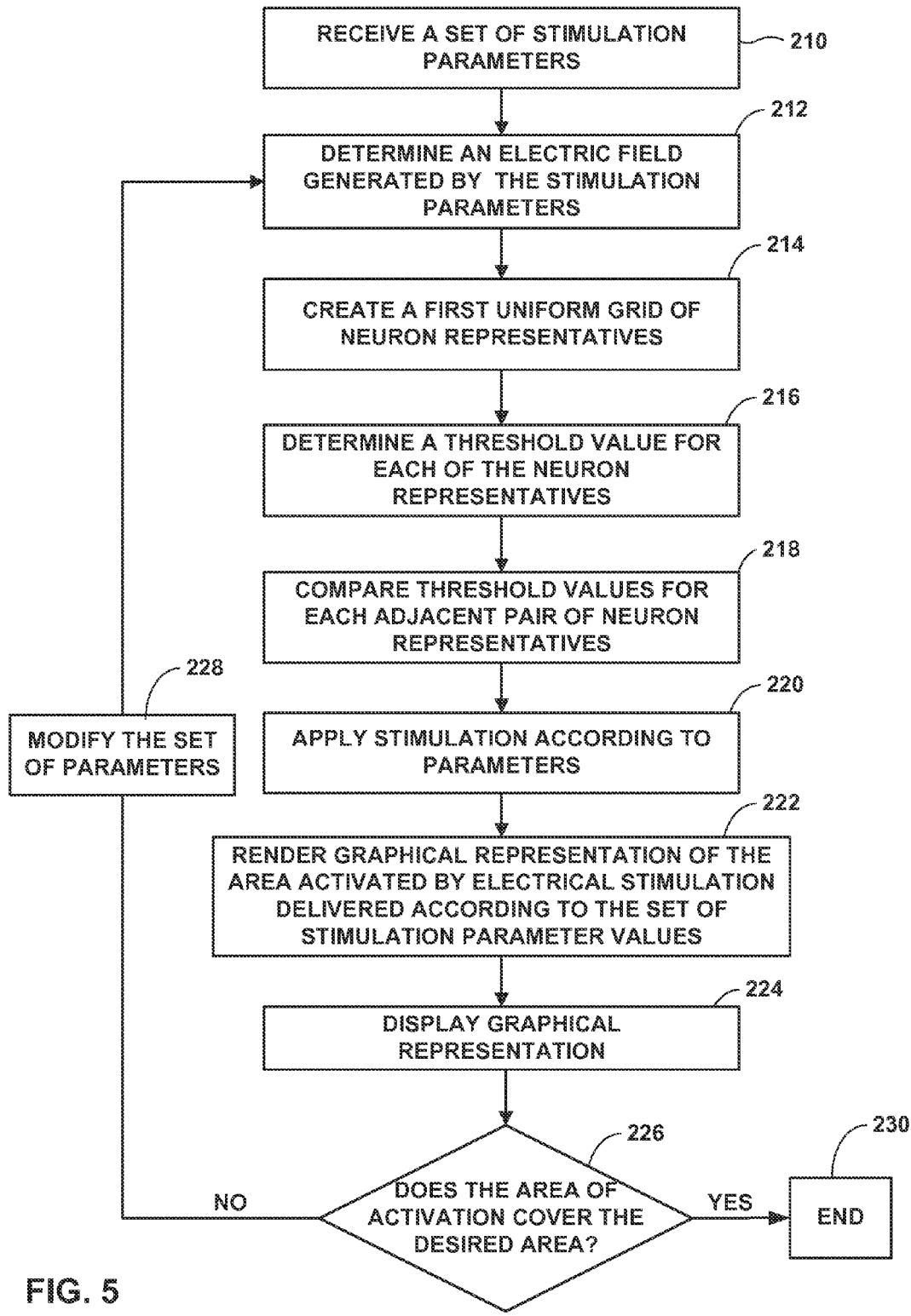
FIG. 5 is a flow chart illustrating an example method of generating a graphical representation of activation based on a non-uniform grid.

FIG. 5 is a flow chart illustrating an example method of displaying an area of activation corresponding to a selected set of stimulation parameter values. Although the method is described as being implemented by external programmer 14, in other examples, the method may be implemented using any computing device. In the technique shown in FIG. 5, processor 80 of programmer 14 receives a set of stimulation parameter values (210) via user interface 84. The set of stimulation parameter values may define, for example, a pulse width and amplitude of a stimulation pulse or a charge level of the pulse. In addition, in some examples, the set of stimulation parameter values includes an electrode combination with which IMD 16 delivers the electrical stimulation signals to patient 12.

Based on the stimulation parameter values of the set and therapy delivery element information 90 stored by memory 82, processor 80 determines an electrical field generated by the stimulation parameters (212). In some examples in which the set of stimulation parameter values includes a single cathode or double cathode unipolar electrode configuration, processor 80 determines the electrical field by at least applying a voltage in an algorithm by setting a boundary to the desired voltage and sets the active electrode to about 0V. For example, a voltage of approximately 1V may be applied to a boundary of a cylinder with a radius of about 50 mm and a height of about 100 mm and centered around the lead representative. The boundary may be selected to ensure a simulation area large enough to capture the area of stimulation. Alternatively, the boundary may be a selected portion of the cylinder that has the same surface area as the active surface area of a medical device.

In some examples in which multipolar stimulation is being simulated, processor 80 assigns a voltage to the anode(s) and assigns 0V to the cathodes(s). The voltage assigned to the anodes may be approximately 1V, for example. The potential distribution generated by the selected electrode combination is calculated from the Laplace equation $\nabla \cdot \sigma \nabla V = 0$, where V refers to extracellular potential and $\sigma$ refers to the electrical conductivity of the medium. The output of this step represents the distribution of voltages within the medium of gray matter surrounding the lead representation.

Figure 10:
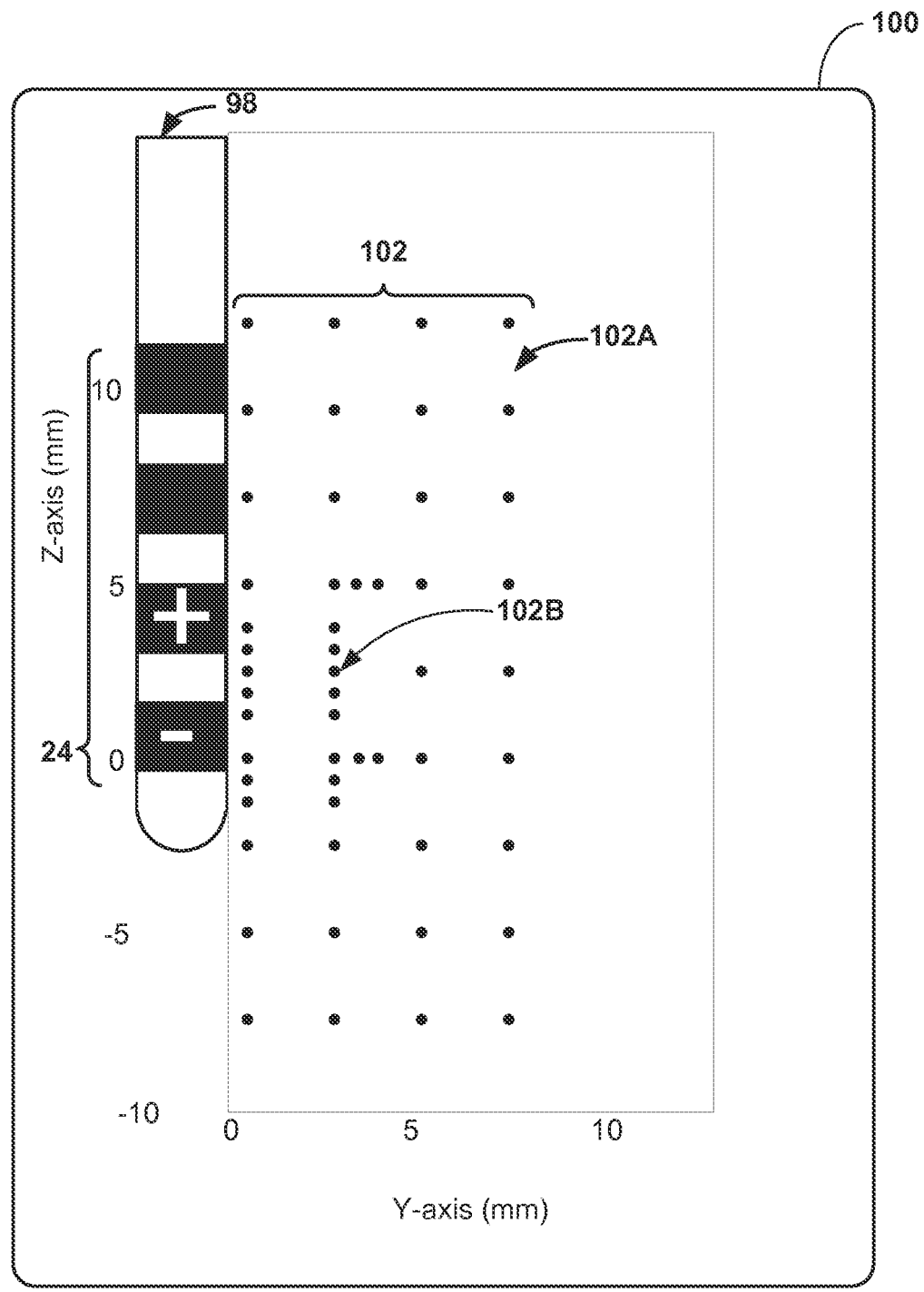
FIG. 10 is a conceptual diagram illustrating an example graphical user interface displaying an example non-uniform grid.
Figure 11:
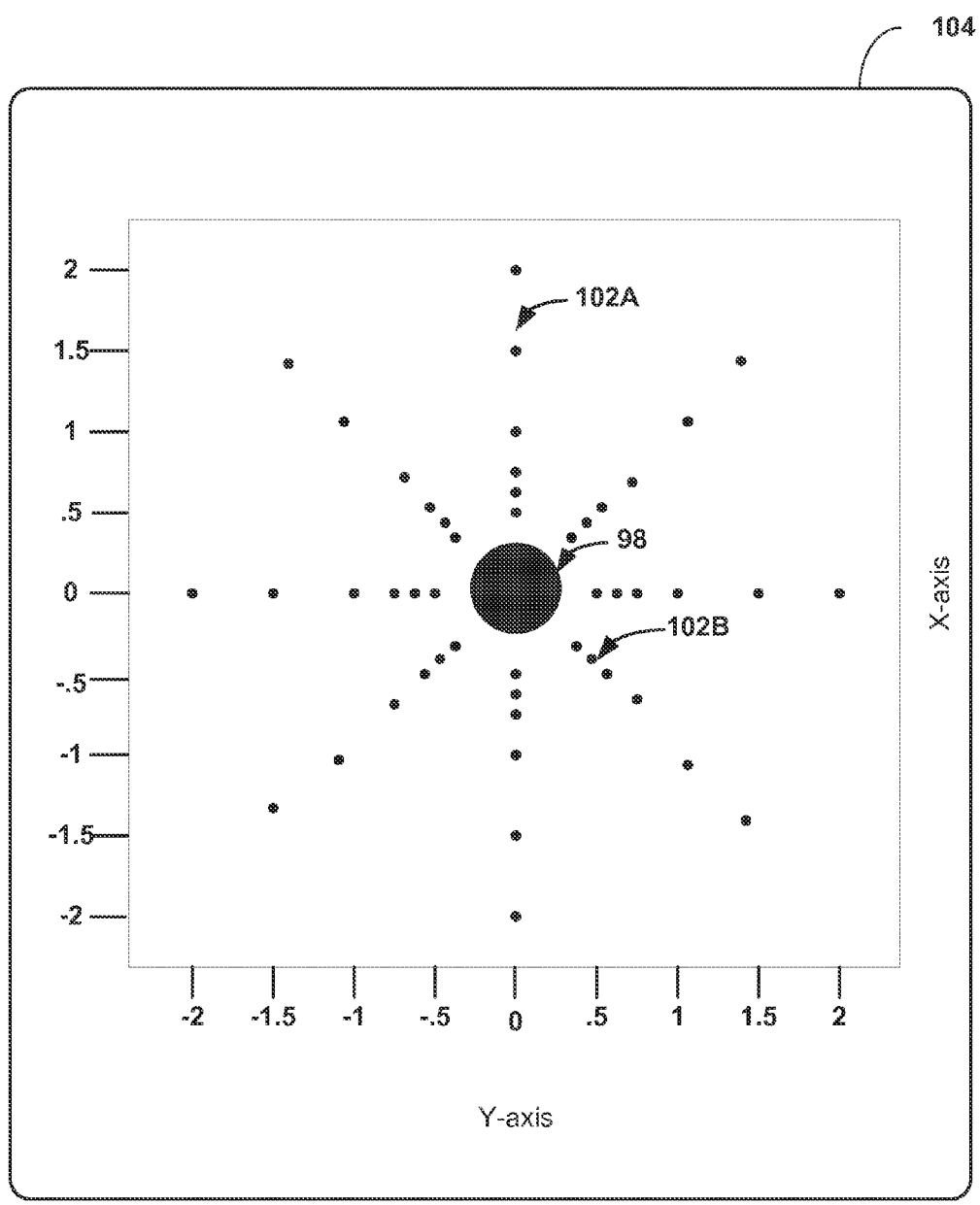
FIG. 11 is a conceptual diagram illustrating an example graphical user interface displaying an example non-uniform grid.
Figure 12:
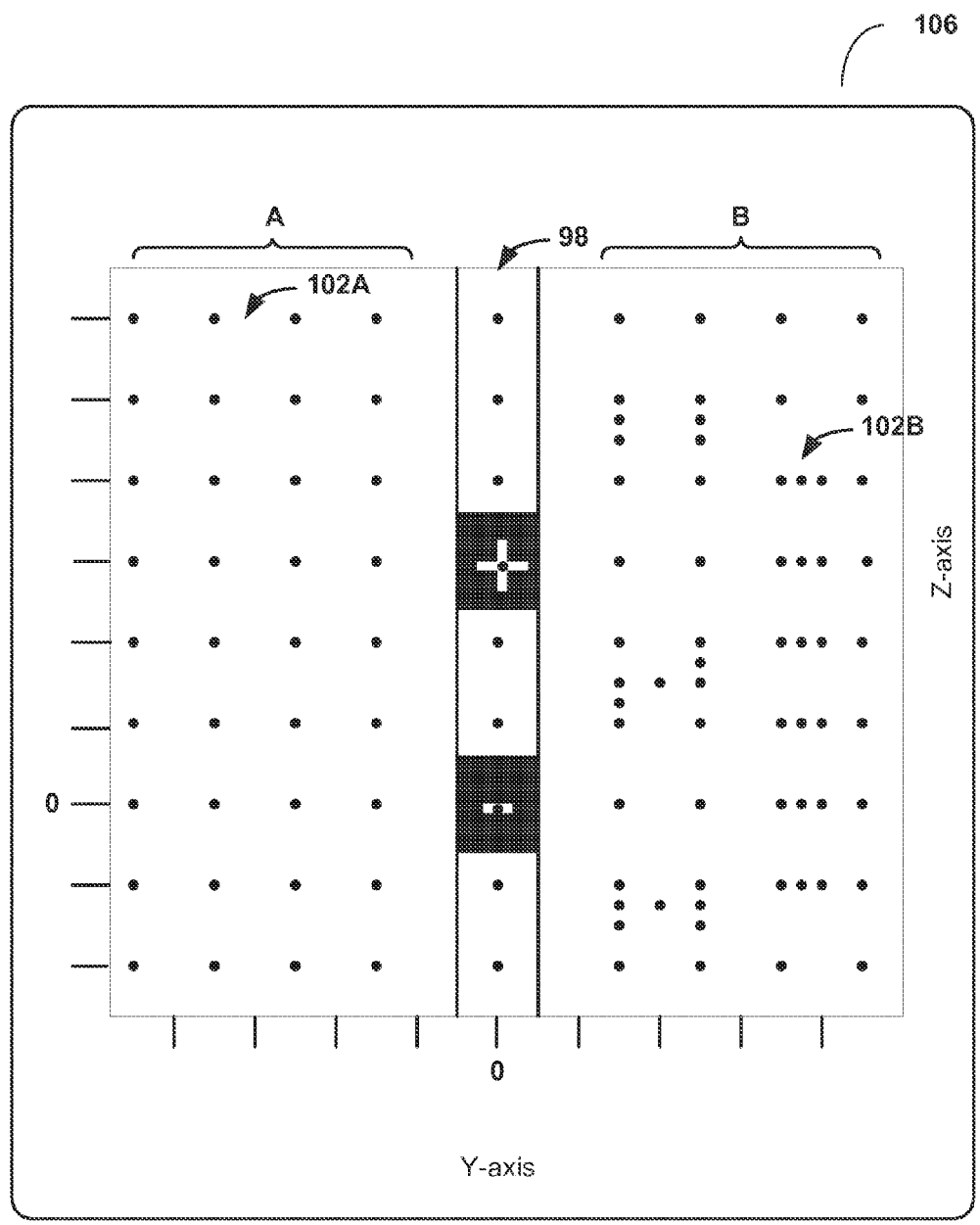
FIG. 12 is conceptual diagram illustrating an example graphical user interface displaying an example non-uniform grid.

In the technique shown in FIG. 5, processor 80 creates a first uniform grid of neuron representatives (214). In some examples, an initial uniform grid of neuron representatives corresponding to a particular lead representation may be saved in memory 82. In some examples, the uniform grid may include neuron representatives spaced approximately 0.25 mm apart, although other initial spacings may also be used. The grid may be visualized as an array of dots, e.g., the dots as shown in FIGS. 10-12, discussed in more detail below, where each dot represents the center of a respective model neuron.

Processor 80 may then determine an activation threshold value for each of the neuron representatives (216) in the first uniform grid of neuron representatives. For a particular neuron representative, the activation threshold value can be, for example, the voltage or current amplitude that when applied by selected electrodes results in a propagating action potential for the neuron representative. In some examples, the activation threshold values may be capped at approximately 10 times a predetermined maximum amplitude value, which can be selected by a user or by automatically processor 80

(e.g., based on the energy output capabilities of IMD 16) and stored by memory 82. For example, if the maximum amplitude for stimulation is 10 mA, then an activation threshold value for a neuron representative may be capped at 100 mA. In other examples, the threshold values may be capped at 3 to 4 times the maximum amplitude value.

Each neuron representative is a model approximating an axon. In some examples, the neuron representation is a multicompartment, double cable, non-linear active module of a mammalian axon. In some examples, the model consists of 21 nodes of Ranvier separated by 20 internodes. Each internode section may consist of 10 compartments each: 2 paranodal myelin attachment segments (MYSA), 2 paranodal fluted main segments (FLUT), and 6 standard intermodal segments (STIN). The nodal sections may contain membrane mechanisms including slow potassium (Ks), fast sodium (Naf), persistent sodium (Nap), and linear leakage conductances in parallel with the nodal capacitance (Cn). In some examples, the neuron representative may include 111 nodes of Ranvier.

In some examples, the activation threshold values for the neuron representative in the first uniform grid may be stored along with the uniform grid in memory 82. In some examples, the activation threshold value may be determined by increasing the stimulation amplitude from 0 V (or Amps, depending on whether IMD 16 is configured for current controlled or voltage controlled electrical stimulation) at given intervals until the neuron representative is activated.

In some examples, processor 80 determines the activation threshold value (216) for each a neuron representative of the grid using a binary search algorithm. For example, processor 80 can apply a starting amplitude to a particular neuron representative. Depending on if the neuron representative was activated or not, processor 80 can increase or decrease the amplitude. In some examples, if increased, the amplitude may be doubled, and if decreased the amplitude may be halfway between 0 and the first amplitude. Processor 80 applies the new amplitude to the neuron representative and, again, depending on whether the neuron representative is activated or not, processor 80 increases or decreases the amplitude. In this subsequent iteration, in the case where processor 80 previously increased the amplitude, if processor 80 decreases the amplitude, then processor 80 may decrease the amplitude to halfway between the previous amplitude and the current amplitude, or, if processor 80 increases the amplitude, then processor 80 may double the amplitude again. In the case where processor 80 previously decreased the amplitude, if processor 80 decreases the amplitude, then processor 80 may decrease the amplitude to halfway between the current amplitude and zero, or, if processor 80 increases the amplitude, then processor 80 may increase the amplitude to halfway between the current amplitude and the previously applied amplitude. This process can continue until processor 80 determines the threshold value for activation within a specified tolerance level.

After the threshold has been determined for each of the neuron representatives of the first grid of neuron representatives (216), processor 80 compares threshold values for each adjacent pair of neuron representatives (218). As described in more detail below with respect to FIG. 6, based on the comparison of the two neuron representative thresholds, processor 80 may determine whether an additional neuron representative should be added to the grid between the two compared neuron representatives. The addition of one or more additional neuron representatives to the grid results in an updated grid, and, in some cases, may result in a non-uniform grid having non-uniformly spaced neuron representatives. In some examples, processor 80 conducts the threshold comparison for any new pairs of adjacent neuron representatives that result from the addition of a neuron representative.

In some examples, the steps of determining the activation threshold value for each neuron representative (216) and comparing activation threshold values for each adjacent pair of neuron representatives (218) may be performed at each of a plurality of pulse widths. For example, the activation threshold values (e.g., stimulation amplitude values) may be determined for each neuron representative at pulse widths ranging from 60-450 µsec. In some examples, the thresholds may be determined at 60 µsec, 90 µsec, 150 µsec, 210 µsec, 330 µsec, and 450 µsec. Thus, in some examples, each neuron representative of the uniform grid is associated with a set of threshold values, where each threshold value corresponds to a respective pulse width. For each pulse width, processor 80 can compare the activation thresholds for each pair of adjacent neuron representatives (218). All of the additional grid points (corresponding to neuron representatives) added for individual pulse widths may be included in the final non-uniform grid of neuron representatives. In some examples, after a new neuron representative has been added to the grid for one pulse width, the activation thresholds may be determined for that neuron representative for all pulse widths, and processor 80 may compare any new pairs of adjacent neuron representatives created by the addition of the new representative for all pulse widths in order to determine whether additional neuron representatives should be added.

After processor 80 determines that the neuron representatives of the grid satisfy the stored criteria (discussed below with respect to FIG. 6), and no new neuron representatives need to be added to the grid to satisfy the criteria, processor 80 runs a simulation of the electrical stimulation (220) using the updated grid. In the example shown in FIG. 5, processor 80 simulates the application of electrical stimulation according to the set of stimulation parameter values (220) using the updated grid. Processor 80 determines whether the electrical current or voltage reaching each of the neuron representatives is sufficient to activate the neuron representative, given the propagation threshold associated with the neuron representative.

Each neuron representative of the grid represents the location of a center of a model neuron. The updated grid includes an increased density of neuron representatives in areas around the border between activation and non-activation relative to the first uniform grid. By increasing the density of neuron representatives where the change in response occurs, finer resolution is achieved in the area where it may be particularly beneficial in order to provide an accurate picture of the area activated by a set of stimulation parameter values. Processor 80 determines whether each neuron representative of the updated grid is activated by stimulation according the set of stimulation parameter values. However, the increased density of neuron representatives results in more calculations than the number of calculations required to determine the activation area using the first uniform grid.

Based on a determination by processor 80 of whether each individual neuron representative would be activated or not by the electrical stimulation provided based on the set of stimulation parameter values, processor 80 renders a graphical representation of the area activated by the electrical stimulation delivered according to a set of therapy parameter values (222).

After the graphical representation has been rendered, processor 80 provides the graphical representation to user interface 84. User interface 84 includes a display (or other visible output) that presents the graphical representation to a user (224). In some examples, the graphical representation may be a 2D image. In some examples, the graphical representation is a 3D image. In some examples, the graphical representation is combined with a graphical representation of a portion of the body of the patient (e.g., the brain) where the stimulation therapy is intended to be delivered. Processor 80 may also present a ruler or other measurement tool (e.g. dragging a line between two points using an input tool such as a finger or stylet and simultaneously displaying the distance between those two points) with the graphical representation in order to help a user judge the size of the activation area or volume.

In the example shown in FIG. 5, based on the graphical representation of the area of activation, processor 80 determines whether the area of activation covers the desired area (226). The desired area is an area that a clinician has determined should be targeted to receive stimulation. The desired area may be all, or some part, or a particular anatomical structure (e.g., a structure of the brain). The clinician may determine the desired area based on a patient's symptoms, for example. In some examples, the desired area may be determined based on patient specific imaging or other data. In some examples, the desired area may be selected based on the patient's individual anatomy. The desired area may also be determined by referencing a database of information related to treatment delivered to other patients with similar symptoms, conditions or disease state.

In some examples, the determination is based on the size of the activation area. The activation area may either be too large or too small, e.g., may activate tissue that is not desired to be activated, or may not activate desired tissue. Thus, in some examples, processor 80 determines whether the activation area overlaps with the desired area by a threshold amount (e.g., 75% to 95%), which may be selected by a user in some examples. In addition, or instead, in some examples, processor 80 may also determine whether the shape of the activation volume is as desired. For example, processor 80 may compare the outline of the activation area to a stored template (e.g., a 2D or 3D template) that indicates the configuration (e.g., shape and size, and, in some cases, location relative to one or more anatomical structures) of the desired activation area, and processor 80 may determine the area of activation covers the desired area in response to determining the generated activation area substantially matches (e.g., matches or nearly matches) the template. Other techniques may also be used to determine whether the area of activation covers the desired area. In some examples, a user may interact with user interface 84 to make the determination.

If the activation area covers the desired area ("YES" branch of block 226), then processor 80 may pause or end the technique shown in FIG. 5, (230), or repeat it for another set of stimulation parameter values. In some examples, processor 80 stores the stimulation parameter set in memory 82 or another memory (e.g., of IMD 16) for later use for therapy delivery by IMD 16. In addition, in some examples, processor 80 stores the graphical representation of the activation area in memory 82 (or another memory) and associates the graphical representation with the set of stimulation parameter values resulting in the graphical representation. In some examples, under the control of processor 80, the set of stimulation parameter values is transmitted from programmer 14 to IMD 16 via telemetry module 86.

In the event that the area of activation does not meet the requirements of the user ("NO" branch of block 226), processor 80 may modify one or more stimulation parameter values of the set (228), e.g., based on a set of rules or in response to user input indicating how the values should be modified. Processor 80 may repeat the steps needed to render a new graphical representation of the activation area that may result from delivery of electrical stimulation according to the modified stimulation parameter values and display the graphical representation to the user. In examples in which the electrode configuration has changed, processor 80 may redetermine the electric field (212), determine the threshold values for each of the neuron representatives (216), and compare threshold values for each adjacent pair of neuron representatives (218). In examples in which only amplitude and/or pulse width have been modified, processor 80 may apply stimulation according to the new parameters (220) without redetermining a new non-uniform grid. The new graphical representation of the activation area may also be stored in memory 82 along with the new set of stimulation parameters that resulted in the new graphical representation. The example method of FIG. 5 may be repeated until an activation area of the appropriate size and shape are created.

Figure 6:
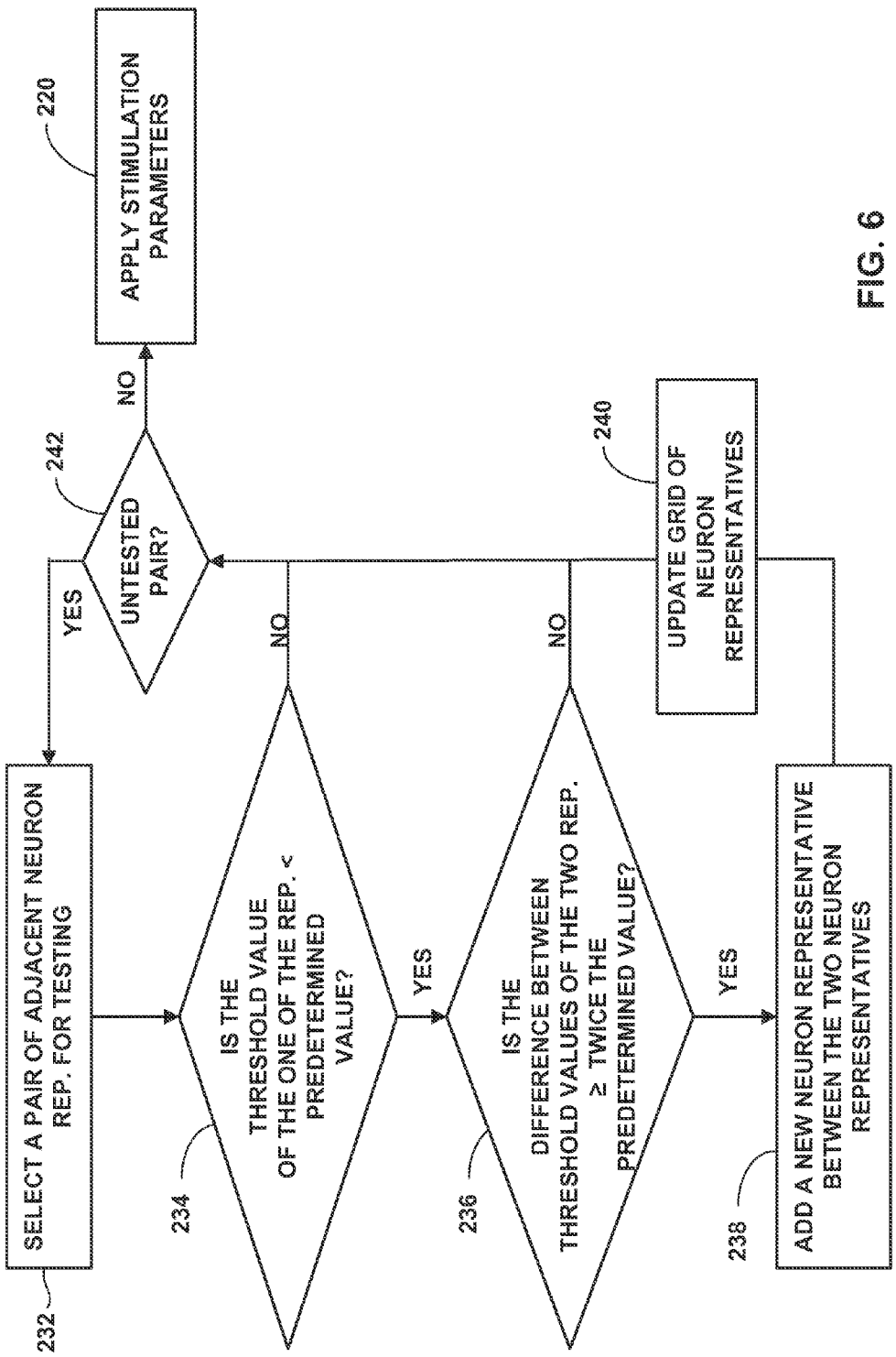
FIG. 6 is a flow chart illustrating in further detail the example method of generating the non-uniform grid of FIG. 5.

FIG. 6 is a flow chart illustrating an example method for generating additional grid points for a non-uniform grid. FIG. 6 explains in more depth example techniques for creating a second (updated) non-uniform grid of neuron representatives based on the comparison of activation threshold values of adjacent pairs of neuron representatives as discussed with respect to FIG. 5.

According to the example of FIG. 6, processor 80 selects a pair of adjacent neuron representatives of a first grid for testing (232). Processor 80 determines whether the activation threshold value of the one of the neuron representatives of the pair is less than a predetermined value (234). In some examples, the predetermined value may be the upper end of desired stimulation amplitude range. For example, the predetermined value may be approximately 30 mA. In other examples, the predetermined value may be approximately 10 mA. If neither of the neuron representatives of the pair has a threshold value less than the predetermined value ("NO" branch of block 234), then processor 80 determines if there is another untested pair (242).

If one of neuron representatives of the pair has a threshold value less than the predetermined value, then processor 80 determines whether the difference between the threshold values of the two neuron representatives is more than twice the predetermined value (236). For example, in one example, processor 80 determines whether the difference between the thresholds of the two neuron representatives of the pair is greater than or equal to approximately 60 mA. In another example, processor 80 determines whether the difference between the thresholds of the neuron representatives is greater than or equal to approximately 20 mA. The use of the two criteria (234, 236) identifies areas of the grid where there is a change from activated to not activated, and where there is a steep change in thresholds surrounding the change from activated to not activated. This allows for modifications to the grid in areas where greater resolution may be useful for determining the activation area, where there may be the most need for greater resolution.

If both criteria are met ("YES" branch of block 236), then processor 80 adds a new neuron representative half way between the two neuron representatives of the selected pair (238). Processor 80 then updates the grid or neuron representatives (240) to include the new representative, along with the threshold value of the new neuron representative. Thus, in some examples, processor 80 determines the threshold value of the new representative.

Processor 80 then determines if there is an untested pair of neuron representatives within the updated grid (242), where "untested" may refer to a pair of adjacent neuron representatives whose activation thresholds have not been compared. If there is an untested pair of neuron representatives, then processor 80 selects a new pair of neuron representatives to test (232). In some examples, where one of the neuron representatives of the pair of adjacent neuron representatives is a new neuron representative (e.g., not part of the first grid and added, e.g., in step 238), processor 80 adds an additional new representative between the new neuron representative and the neuron representative with a threshold value less than the predetermined value in response to determining the difference between the new neuron representative and the neuron representative with the activation threshold value less than the predetermined value is more than twice the predetermined value. Processor 80 may add an additional new neuron representative between the new neuron representative and the second neuron representative of the original pair of neuron representatives in response to determining the activation threshold value of the new neuron representative is less than the predetermined value and the difference between the activation threshold value of the new neuron representative and the second neuron representative of the original pair of neuron representatives is still greater than or equal to twice the predetermined value.

Figure 7:
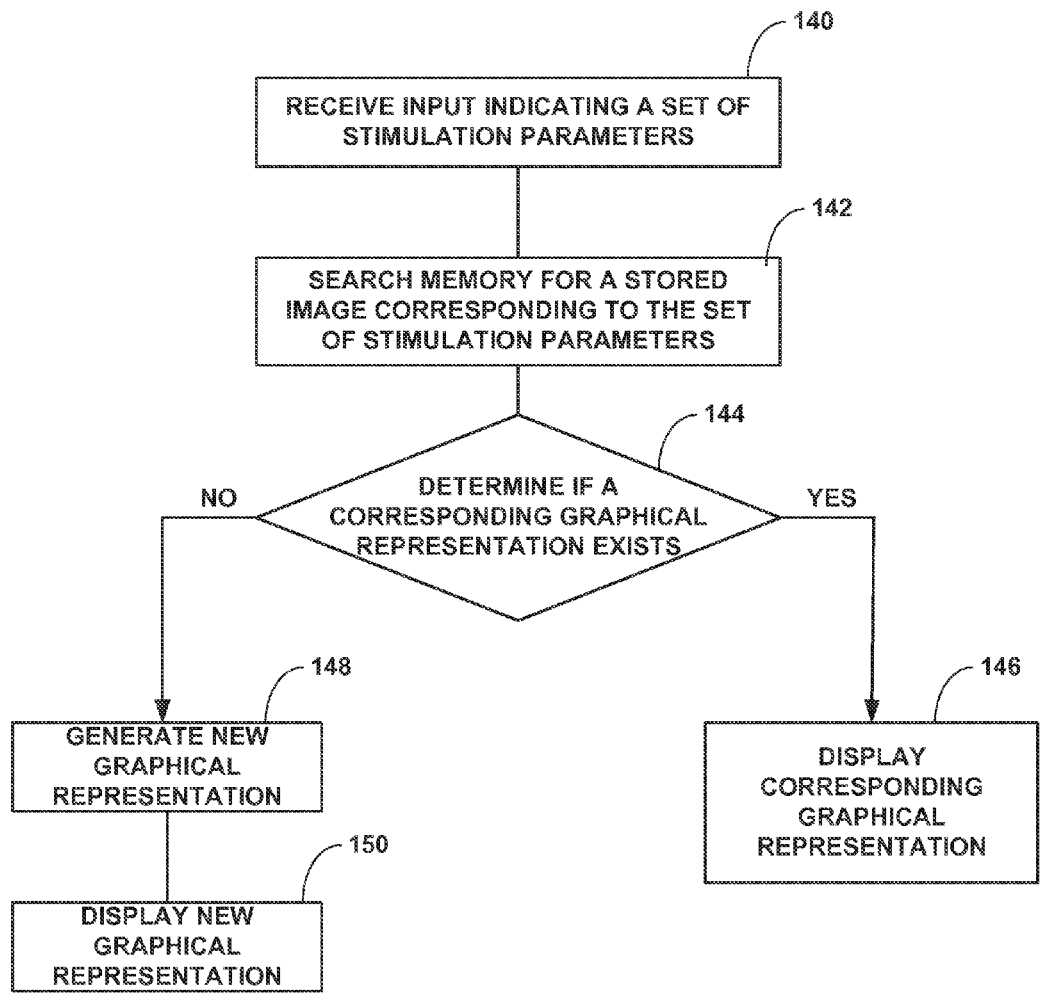
FIG. 7 is a flow chart illustrating an example method of presenting a graphical representation of an area of activation based on a non-uniform grid.

If there are no untested pairs ("NO" branch of block 242), then processor 80 applies a set of stimulation parameter values (220) to the updated grid of neuron representatives in order to determine the activation area associated with the set, e.g., in accordance with the example technique described with respect to FIG. 7. In some examples, not shown and as discussed above with respect to FIG. 5, processor 80 may repeat the process of adding new neuron representatives for a number of pulse widths. For example, for each of a plurality of pulse widths, processor 80 may compare the activation thresholds the neuron representatives of a selected pair of neuron representatives and add additional neuron representatives based on the comparison (e.g., blocks 234 and 236). Processor 80 may then apply the set of stimulation parameter values to an updated grid that includes the new neuron representatives from each of the pulse widths tested.

While the current example describes the addition of a new neuron representative as requiring satisfaction of both checks 234 and 236, in other embodiments, a new neuron may be added if only check 236 is satisfied. Alternatively, an additional check could be added that must also be satisfied before another neuron is added. Thus, FIG. 6 is one example according to the disclosure.

FIG. 7 is a flow chart illustrating an example method of generating and displaying a graphical representation of an activation area. Programmer 14, and in particular, processor 80, receives user input indicating a set of stimulation parameters (140). For example, the user may select the stimulation parameter values of the set by providing input via user interface 84. The input may indicate specific values for one or more stimulation parameters in the set, select the set from a list of predetermined sets of stimulation parameter values, or indicate the set using any other suitable technique. In some examples, the stimulation parameter values of the set may be default parameters of IMD 16, may be the parameters previously set on IMD 16, or may otherwise be stored by memory 82, and processor 80 may automatically determine the set of stimulation parameter values, e.g., independent of user input.

Processor 80 searches memory 82 for a stored graphical representation corresponding to the set of stimulation parameter values (142). Processor 80 determines if a corresponding graphical representation exists (144), e.g., is stored by memory 82 based on the search. For example, processor 80 may determine that a corresponding graphical representation exists if memory 82 includes a graphical representation associated with the set of stimulation parameter values. If a graphical representation exists, then processor 80 retrieves the graphical representation from memory 82 and presents the graphical representation to the user via a display of user interface 84 (146).

If there is no corresponding graphical representation, then processor 80 generates a new graphical representation (148). The new graphical representation may be generated as discussed above with respect to FIGS. 5 and 6. In some examples, a portion of the process of generating the new graphical representation for the set of stimulation parameter values may already be saved. For examples, a first uniform grid of neuron representatives may be saved for a particular electrode configuration. In other examples, a second, non-uniform grid based on the threshold comparisons may be saved in memory 82 for the particular electrode configuration. In such examples, processor 80 may need only apply stimulation according to the remaining stimulation parameter values, e.g., amplitude and pulse width, to generate the graphical representation of the activation area.

Based on which neuron representatives would be activated, as indicated by a grid of neuron representatives and the stimulation parameter values of the set, processor 80 generates a new graphical representation (148) of the area of activation. Processor 80 may then present the graphical representatives via a display of user interface 84 (150). In some examples, the new graphical representation may include graphical representation of a lead representative, a graphical representation of the area that is activated, and a graphical representation of the portion of the brain anatomy in which the stimulation will be provided. In some examples, the graphical representation of the brain anatomy includes an outline of the desired area for stimulation. In some examples, the graphical representation of the brain anatomy includes an outline of the undesired area for stimulation. In addition, or instead, processor 80 may display one or more other graphical guides with the graphical representation of the activation area, where the graphical guides may be selected to aid the user's visualization of the activation area that may result from the delivery of electrical stimulation according to a set of stimulation parameter values. In some examples, processor 80 selects the type of graphical guides to display based on user input received via user interface 84.

In some examples, processor 80 generates the new graphical representation (148) using linear interpolation from a plurality of previously stored graphical representation and associated data for stimulation parameter values near those of the set of stimulation parameter values. For example, memory 82, and in particular stored graphical representation 94, may include graphical representations and associated data for a plurality of pulse widths, e.g., 60 μsec, 90 μsec, 210 μsec, 330 μsec, and 450 μsec at an amplitude of 1 mA. If a stimulation parameter set includes a pulse width of 75 μsec at an amplitude of 1 mA, then processor 80 may linearly interpolate between the graphical representations of activation areas associated with the 60 and 90 μsec pulse widths, e.g., using the activation threshold data, in order to generate a graphical representation of the approximate area or volume of activation. In other examples, memory 82 may store graphical representations and associated values for a plurality of values of some other stimulation parameter. For example, graphical representations may be associated with stimulation charge levels, pulse frequency, or pulse amplitude.

Figure 8:
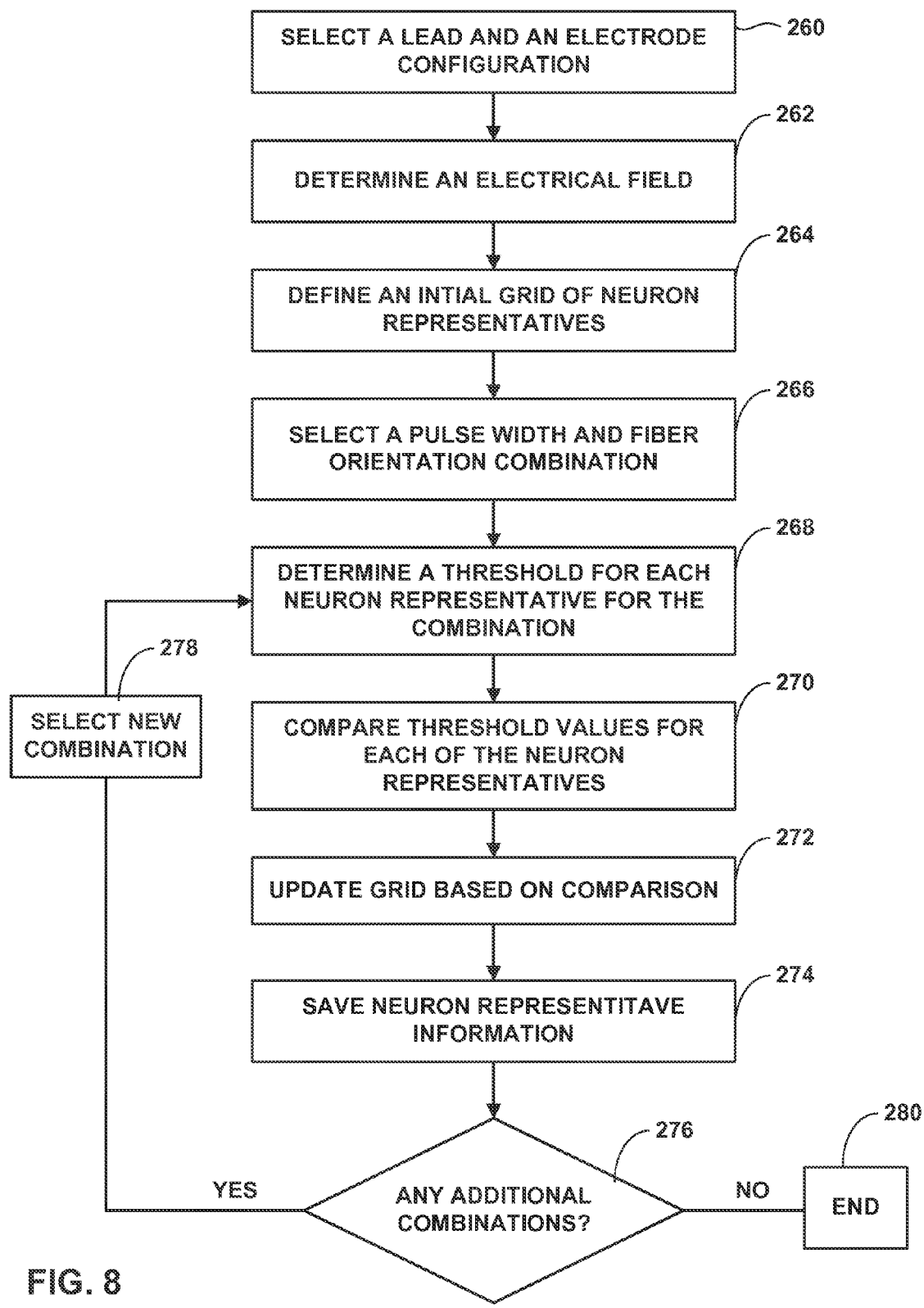
FIG. 8 is a flow chart illustrating an example method of generating a non-uniform grid for generating an area of tissue activated.

FIG. 8 is a flow chart illustrating an example method of generating a plurality of sets of activation thresholds for a grid of neuron representatives. Each set of activation thresholds corresponds to a different combination of pulse width and fiber orientation. Processor 80 can select a set of activation thresholds to generate a graphical representation of an activation area for a particular lead or other therapy deliver element, electrode configuration, and set of therapy parameter values. In some examples, a user, such as a physician or other clinician, may use programmer 14 to program therapy parameters for delivery of electrical stimulation, by IMD 16, to patient 12 via one or more electrodes. Processor 80 of programmer may load a look-up table from memory 82 that corresponds to a desired lead and electrode configuration. In some examples, the look-up table is stored in graphic processing data 92. The method of FIG. 8 may be used to generate the look-up table stored in memory 82 of programmer 14.

During generation of the look-up table, processor 80 selects a therapy delivery element configuration (260). For example, processor 80 may select a lead and electrode configuration based on user input received via user interface 84, where the user input may indicate a particular lead, electrode configuration, or both. In some examples, the lead selected corresponds to an implanted lead 20. The lead may be Medtronic Lead Model 3387, Model 3389 or Model 3391, which are each available from Medtronic, Inc. of Minneapolis, Minn., for example. Processor 80 can select any suitable electrode configuration, whether monopolar, bipolar, or multipolar configuration. For example, processor 80 may select a single electrode 24 or 26 as cathode for monopolar stimulation. In examples in which the electrode configuration is a bipolar configuration, the anode electrode and cathode electrode can be on the same lead and next to each other or separated by one or more electrodes. In examples in which the electrode configuration is a multipolar configuration, two electrodes may be programmed as cathode electrodes separated by an electrode programmed as an anode electrode, or two electrodes 24 may be programmed as anodes, and one electrode 24 may be programmed as a cathode. Other electrode configurations are also contemplated and may also be used with the devices, systems, and techniques described herein.

Processor 80 may determine an electrical field model (262) for the selected lead and electrode configuration, where the electrical field model indicates the electrical potential distribution generated in a particular medium. For example, for a single or double cathode monopolar electrode configuration, processor 80 can apply a voltage of −1 V by setting a boundary to approximately 0 V and the active electrode(s) to −1 V. For other electrode configurations, such as bipolar or multipolar configurations, processor 80 may assign 0 V to the anode(s) and −1 V to the cathode(s). The potential distribution generated in the tissue medium is calculated from the Laplace equation $\nabla \cdot \sigma \nabla V = 0$, where as discussed above, V refers to the extracellular potentials and σ refers to the electrical conductivity of the medium. The output of the calculation is a field solution that approximates the distribution of gray matter in a patient.

Programmer 80 defines an initial grid of neuron representatives (264). In some examples, the initial grid includes neuron representatives spaced approximately 0.25 mm apart and oriented such that the fibers are substantially perpendicular to the longitudinal axis of the lead. For ease of description, the perpendicular orientation is defined as a 0 degree orientation. In some examples, for the initial grid, each neuron representative may include 111 nodes and 1221 compartments. The potential exported from the electric field model is then interpolated along each compartment of each model neuron.

Processor 80 may select a combination of a therapy parameter value and fiber orientation (266). In some examples, processor 80 may select a pulse width and fiber orientation. For example, the pulse width may be one of 60 μsec, 90 μsec, 150 μsec, 210 μsec, 330 μsec, or 450 μsec. In addition, processor 80 can select the fiber orientation from a set of predetermined angles, e.g., angles from about 0 degrees (°) to about 90° at 10° increments (0°, 10°, 20°, 30°, 40°, 50°, 60°, 70°, 80°, and 90°). In other examples, based on the therapy parameters, processor 80 may select a combination of waveform shape and fiber orientation, or a combination of pulse width, frequency and fiber orientation. Processor 80 runs simulations to determine an activation threshold for each neuron representative for the combination (268). In examples where the combination is of pulse width and fiber orientation, the activation threshold is stimulation amplitude. In examples, where the combination is pulse shape and fiber orientation, the activation threshold may be a stimulation charge value. In examples where the combination is of pulse width, frequency and fiber orientation the activation threshold may be either stimulation amplitude or stimulation charge. The activation threshold may be determined by, for example, applying successively higher amplitudes or pulse charges to a neuron representative until the neuron representative is activated. Activation may be determined by the transmembrane potential reaching 0 mV. In some examples, the amplitude applied in determining the activation threshold may be capped at 100 mA in order to reduce the time of computation. In some examples, the maximum applied amplitude during computation of neuron representative thresholds may be selected based on a maximum amplitude of stimulation applied to a patient in a particular area of the body.

For each pair of neuron representatives, processor 80 compares activation threshold values for each of the neuron representatives (270). The comparison may be made as discussed in more detail above with respect FIG. 6 which discusses a method of comparing thresholds and determining whether to add an additional neuron representative between the compared neuron representatives. Processor 80 updates the grid based on the comparison (272), e.g., as described with respect to FIG. 6. After the grid is updated, processor 80 saves the neuron representative information for each neuron representative of the updated grid (274) in memory 82 (or a memory of another device). In some examples, the updated grid may be stored in a look-up table. The grid is associated with the combination of pulse width and fiber orientation within the look-up table. The grid may include an activation threshold for each of the neuron representatives within the updated grid.

In the technique shown in FIG. 8, processor 80 determines whether there are additional combinations of pulse width and fiber orientation for which to determine propagation thresholds (276). In response to determining there are additional combinations ("YES" branch of block 276), processor selects another combination (278). For the new combination, processor 80 determines a propagation threshold for each neuron representative of the grid (268) and updates the grid accordingly (270, 272). If there are no additional combinations of pulse width and fiber orientation for which to determine propagation thresholds ("NO" branch of block 276), then processor 80 may end the technique shown in FIG. 8. In some examples, the completed file or look-up table is saved. The file or look-up table may be associated with the lead time and electrode configuration used to generated the file or look-up table.

Figure 9:
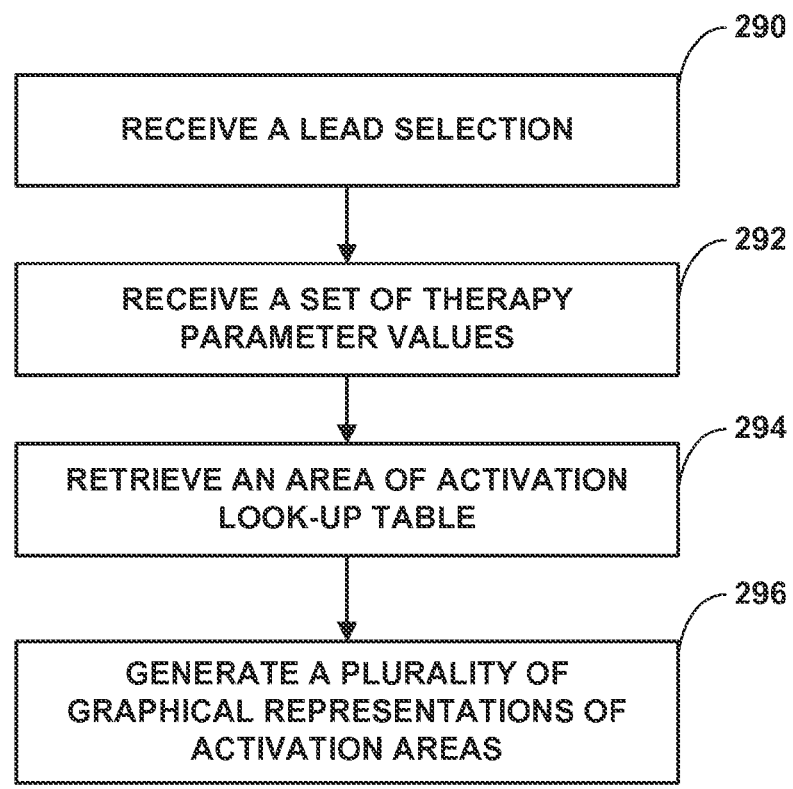
FIG. 9 is a flow chart illustrating an example method of generating an area of tissue activated based on a non-uniform grid.

FIG. 9 is a flow chart illustrating an example method of generating an area of activation based on a non-uniform grid. In some examples, processor 80 may receive a therapy delivery element selection (290) from a user via user interface 84. In some examples, the lead selection may include a lead type and an electrode configuration. Processor 80 may also receive a set of therapy parameter values (292) via user interface 84. The set of therapy parameter values may include a pulse width and amplitude (current amplitude or voltage amplitude).

Processor 80 may retrieve an area of activation look-up table (294) from memory 82 based on the lead selection and set of therapy parameter values. The area of activation look-up table may include an activation threshold for each of a plurality of neuron representatives. In some examples, the area of activation look-up table may include a plurality of activation thresholds for each of the neuron representatives with a grid. The file may include a threshold for a number of pulse width and fiber orientation combinations.

Processor 80 may generate a plurality of graphical representations of activation areas (296) based on the area of activation look-up table. Processor 80 may generate the plurality of graphical representations of the activation areas for the set of therapy parameter values received. In some examples, each of the activation areas of the plurality may correspond to a different fiber orientation. The different graphical representations may be generated from a different set of activation thresholds. Each set of activation thresholds is comprised of one activation threshold for each neuron representative of a grid and is associated with a fiber orientation. In some examples, the set of activation thresholds is associated with at least one therapy parameter value in addition to a fiber orientation. For example, a set of activation thresholds may constitute either the amplitude of stimulation needed to activate each neuron representative, or the charge needed to activate each neuron representative. The sets of activation thresholds in examples where the activation thresholds are amplitudes may be associated with a pulse width and fiber orientation, for example. The sets of activation thresholds in examples where the activation thresholds are charges may be associated with a stimulation waveform shape and fiber orientation, for example. In some examples, each fiber orientation is associated with a different set of activation thresholds for the neuron representatives of a grid.

In some examples, for a particular pulse width, processor 80 determines an activation threshold for each neuron representative for each of a plurality of fiber orientations. Processor 80 then ranks the activation thresholds corresponding to each fiber orientation from low threshold to high threshold for each neuron representative. Processor 80 generates a grouping of thresholds with the same ranking from low threshold to high threshold results based on the probability of activation for the neuron representatives of the grid. For example, the higher the activation threshold of a neuron, the lower the probability of activation of the neuron in response to electrical stimulation according to a particular stimulation parameter set. Processor 80 can generate activation areas for each grouping of activation thresholds of a plurality of groupings, where each grouping may include the activation thresholds of the same rank. In this way, in some examples, the plurality of areas of activation may correspond to selected ranks, and each of the areas of activation may indicate different probabilities of activation. The grouping of activation thresholds having the highest activation thresholds may result in the relatively smallest activation area due to the lower probability of neuronal activation in response to electrical stimulation according to a particular stimulation parameter set, while the grouping of activation thresholds having the lowest activation thresholds may result in the relatively largest activation area due to the higher probability of neuronal activation.

Processor 80 can generate the activation areas for the rankings selected by a user via user interface 84. In other examples, processor 80 selects ranks based on a preprogrammed selection of ranks. In examples in which activation thresholds were determined for fiber orientations at 10 degree increments from 0 degrees to 90 degrees, this results in 10 different rankings, which may correspond to 10 different areas of activation. In some examples, the higher the ranking, the lower the probability of activation. Thus, a ranking of 10 indicates that for a neuron representative that is activated in response to electrical stimulation according to a particular stimulation parameter set, all fiber orientations are activated, and a ranking of 1 indicates that, for a particular neuron representative activated in response to electrical stimulation according to the same stimulation parameter set, only a few orientations (or one fiber orientation) are activated.

Figure 15:
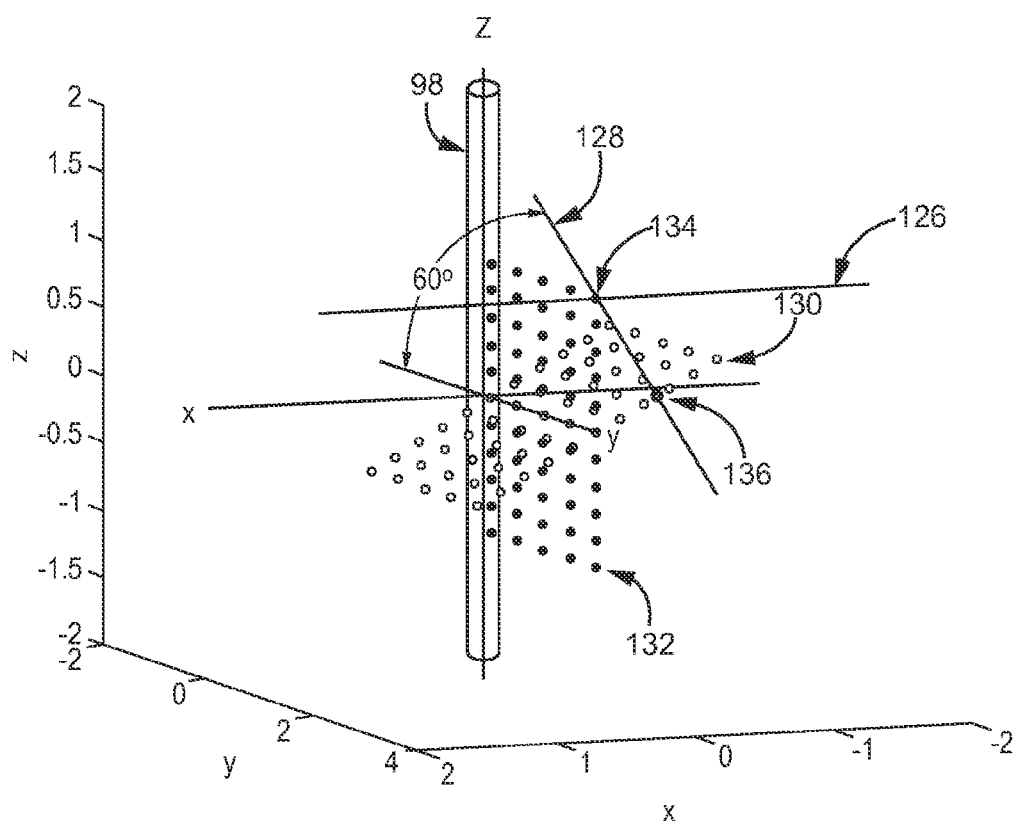
FIG. 15 is a conceptual diagram illustrating the connection between the thresholds of various neuron representatives at different angles of fiber orientation may be connected.

In one example, processor 80 ranks activation thresholds by angle of orientation of the fibers of the neuron representatives, such that a ranking of 10 corresponds to the thresholds of axons oriented substantially perpendicular to the longitudinal axis of the lead (0 degrees with respect to the Y-axis), which may result in relatively highest activation thresholds, while a ranking of 1 correspond to the thresholds of axons oriented substantially parallel to the longitudinal axis of the lead (90 degrees with respect to the Y-axis), which may result in the relatively lowest activation thresholds. However, in some configurations such as the double cathode configuration, axons that are oriented perpendicular to the longitudinal axis of the lead may have lower thresholds than those oriented parallel to the longitudinal axis of the lead at some locations due to a decrease in the activating function along the lead when the axons are oriented parallel versus perpendicular to the longitudinal axis of the lead. Thus, in some examples, each ranking may not include all of the same fiber orientation. For example, as shown in FIG. 15, and discussed in more detail below, a particular neuron representative with a given fiber orientation may have a lower threshold because the angle of the fiber orientation results in a point along the fiber wherein the neuron is closer to the activated electrode.

FIG. 10 is a conceptual diagram illustrating an example GUI displaying an example non-uniform grid generated in accordance with techniques described herein. The GUI shown in FIG. 10 may be generated by processor 80 and presented via a display of user interface 84. The graphical representation displayed on graphical user face is an X-Z planar view 100 including a lead representative 98, which may be representative of lead 20A. A longitudinal axis of lead representative 98 extends in the Z-axis direction, which is substantially orthogonal (orthogonal or nearly orthogonal) to the X-axis direction. The lead representative includes an indication, such as the plus and minus signs shown in FIG. 10, of which electrodes 24 are being used to provide stimulation, as well as the polarity of the electrodes.

The graphical representation also includes neuron representatives 102. As shown in FIG. 10, neuron representative groups 102A and 102B have different spacing between each of the neuron representatives within the groups. Neuron representative group 102B includes neuron representatives added based on a comparison of the threshold values of existing neuron representatives in the manner described above, e.g., with respect to FIG. 6. Accordingly, the density of neuron representatives in area 102B may be greater than in other areas of neuron representatives 102, or within a uniform grid. In some examples, the area containing neuron representatives 102B may be the area in which processor 80 determined there to be a relatively large change in threshold values in the original uniform grid. In examples such as the one shown in FIG. 10, where stimulation is provided by a bipolar configuration, the area between the two active electrodes can be more likely to include additional neuron representatives 102, as illustrated by group 102B.

The remaining activation area being modeled by processor 80 includes neuron representative group 102A. Neuron representatives of group 102A have a greater distance between each of the neuron representatives of group 102B. The use of more closely spaced neuron representatives in the areas where a relatively large change in activation threshold values occurred allows for greater resolution in the area near the border between the neuron representatives that are activated by the stimulation pulse and those that are not. When a uniform grid is used, the appropriate resolution may not be achieved, and the border of an activation area presented to a user may not be accurate.

In some examples, each of the neuron representatives 102 is associated with a variety of information. For example, each neuron representative may be a neuron model that includes information regarding neuron diameter, and model of the mechanisms of the neuron membrane. In some examples, the neurons are modeled as multi-compartment cables with non-linear membrane mechanisms that include fast and persistent sodium, potassium and leakage conductances. Processor 80 uses the locations of neuron representatives 102 as shown on graphical user interface 100 along with various threshold values associated with each neuron representatives, and achieved from actual stimulations, to determine whether a particular neuron representative is activated in response to stimulation delivered via a particular set of stimulation parameter values. Based on which neuron representatives are activated, processor 80 generates an area of activation. In an example such as FIGS. 4B and 4C, the area of activation is a contour plot.

The closer spacing of neuron representative group 102B allows for greater definition, and a more accurate depiction, of the activation area than if the wider spacing of neuron representative group 102A was used throughout the grid. The closer spacing of the neuron representatives 102B is closer than the spacing of neuron representatives 102A. By determining the activation area based on a grid including a greater number of neuron representatives, processor 80 may generate an activation area that more accurately depicts the transition from activated neurons to inactivated neurons. However, an increase in neuron representatives in the area with neuron representatives 102B may require processor 80 to perform a greater number of calculations in order to determine the activation area, which may slow down processing time. The identification of areas with rapid changes in activation threshold value to add additional representatives, and consequently finer resolution, allows for a balance between resolution and computational intensity. For example, as discussed in FIGS. 5, 6, and 8, areas of rapid change in activation threshold may be detected based on a comparison of the activation thresholds of adjacent neuron representatives.

FIG. 11 is a conceptual diagram illustrating an example GUI displaying an example non-uniform grid generated in accordance with techniques described herein. The GUI shown in FIG. 11 may be generated by processor 80 and presented via a display of user interface 84. FIG. 11 shows a view of the non-uniform grid in the X-Y planar view 104, where the X-axis is substantially orthogonal to the Y-axis. Lead representative 98 is at the center of neuron representatives 102. In X-Y planar view 104, a longitudinal axis of lead representative 98 extends in the Z-Axis direction, which is perpendicular to the plane shown in X-Y view 104. Neuron representatives in group 102B are more closely spaced than neuron representatives in group 102A. As shown in FIG. 11, in some examples, the spacing between neuron representatives may not be the same in every direction. For example, the spacing between a neuron representative and the nearest neuron representative in the X, Y, and Z directions may be different. However, the spacing in at least one direction is closer in areas with a rapid change in activation threshold values.

FIG. 12 is a conceptual diagram illustrating an example GUI displaying an example non-uniform grid in accordance with techniques described herein. The GUI shown in FIG. 12 may be generated by processor 80 and presented via a display of user interface 84. FIG. 12 shows a view of the non-uniform grid in the X-Z planar view 106 for a grid generated based on an electrode configuration having a single anode and a single cathode, both a part of lead representative 98 (the longitudinal axis of lead representative 98 extends in the Z-axis direction). The graphical representation includes a lead representative 98 including electrodes. FIG. 12 includes a portion of the grid on side A and a portion of the grid on side B. The grid on side A is a uniform grid with neuron representatives 102A that illustrate the neuron spacing prior to the adding additional neuron representatives 102B. Side B illustrates a possible final grid wherein additional neuron representatives 10B have been added to the initial uniform grid, e.g., using the techniques described above with respect to FIG. 5. As with FIGS. 10 and 11, the additional neuron representatives 102B are in areas where a steep change in threshold values was found.

Figure 13A:
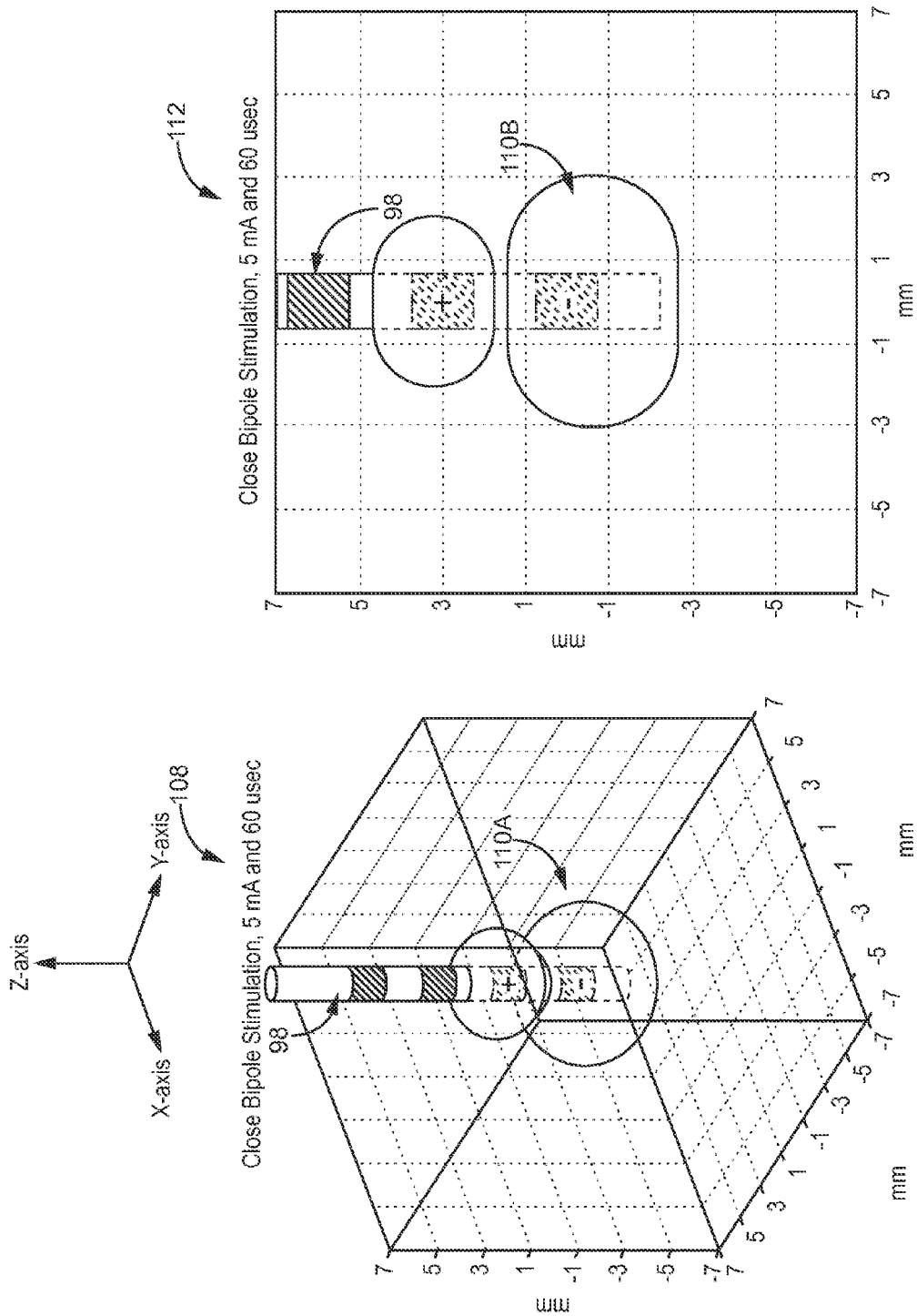
FIG. 13A is a conceptual diagram illustrating an example graphical user interface displaying an example graphical representation of an activation area generated based on a non-uniform grid.

FIG. 13A is a conceptual diagram illustrating an example GUI displaying example graphical representations of example activation areas generated based on a non-uniform grid in accordance with techniques described herein. The GUI shown in FIG. 13A may be generated by processor 80 and presented via a display of user interface 84. In the example of FIG. 13A, the GUI includes two graphical representations of activation areas, each generated from the same underlying data and for the same set of stimulation parameters. Graphical representation 108 is a 3D image depicting volume of activation 110A. Volume of activation 110A extends around lead representative 98 which includes an indication of which electrode is acting as an anode and which electrode is acting as a cathode. In the example illustrated, the stimulation parameters include a stimulation amplitude of 5 mA and a stimulation pulse width of 60 μsec.

The GUI shown in FIG. 13A also includes graphical representation 112, which is a 2D graphical representation of an activation contour 110B. The activation contour 110B lies in the Z-X plane (substantially orthogonal X-Y-Z axes are shown in FIG. 13A) and represents the portion of activation volume 110A in the Z-X plane. In some examples, the graphical representation depicting the volume of activation 110A may be generated by replicating the graphical representation of activation area 110B at a plurality of rotational positions, e.g., evenly spaced about the available 360 degrees, around the lead representative 98 in order to create the 3D depiction of activation volume 110A.

Figure 13B:
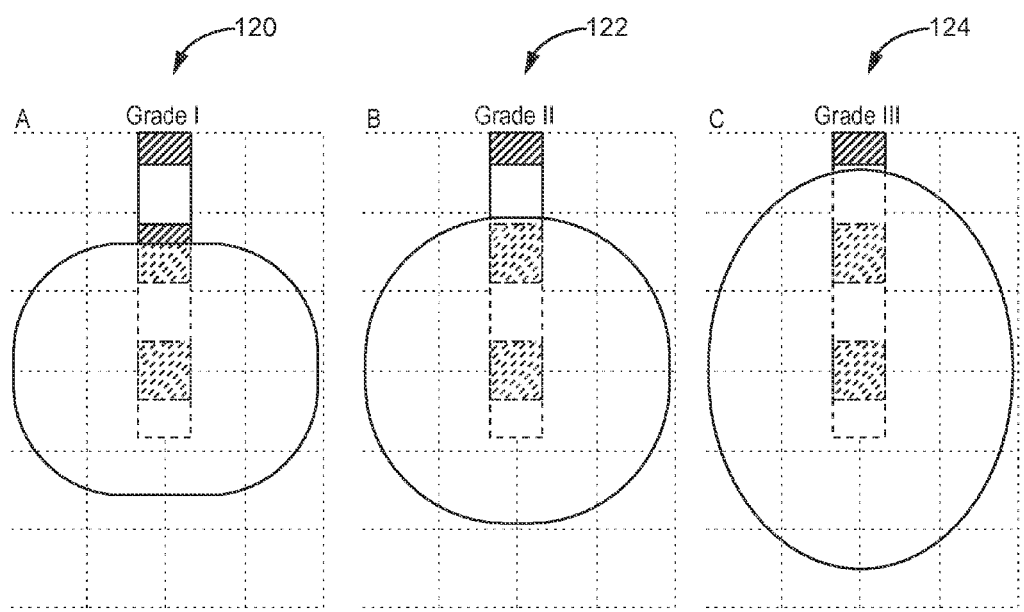
FIG. 13B is a conceptual diagram illustrating an example graphical user interface displaying an example graphical representation of an activation area for a plurality of probability groupings.

FIG. 13B is a conceptual diagram illustrating an example GUI including a plurality of activation areas 120, 122, 124. The GUI shown in FIG. 13B may be generated by processor 80 and presented via a display of user interface 84. The plurality of activation areas are generated by processor 80 for the same set of therapy parameter values, but for neuron representatives having different fiber orientations. In some examples, processor 80 renders activation areas 120, 122, 124 for example, based on an array of activation thresholds. In some examples, the array of activation thresholds includes a single activation threshold for each of the neuron representatives. The activation thresholds within the array may be selected based on a particular fiber orientation, or ranking of activation thresholds associated with each of the neuron representatives. Activation areas 120, 122, 124 are rendered based on array of X, Y, and Z coordinates, where (0, 0, 0) corresponds to the geometric center of an activated electrode, and an array of indices of the vertices defining the triangular defining the surface of the activation volume.

In some examples, three activation areas 120, 122, 124 may be displayed side by side, as shown in FIG. 13B. In some examples, the shape of the area of activation may change depending on the orientation of the fibers relative to the lead (the longitudinal axis of the lead corresponding to the Z-axis) and the electric field. The change in shape is illustrated by activation areas 120, 122, and 124. In the example GUI shown in FIG. 13B, each of the areas of activation are labeled with a grade: Grade I (120), Grade II (122) and Grade III (124). Each grade may correspond to a different fiber orientation or a different probability grouping/ranking of activation threshold values associated with a neuron representative. For example, Grade I activation area 120 may correspond to an activation area generated by processor 80 based on a grouping of the highest activation thresholds for each of the neuron representatives of a particular grid. As another example, Grade I activation area 120 may correspond to an activation area generated based on the activation thresholds corresponding to a 0 degree fiber orientation with respect to the Y-axis. In this example, the activation thresholds corresponding to neuron representatives having the 0 degree fiber orientation may have different rankings, e.g., some may be the highest activation thresholds relative to the activation thresholds corresponding to other fiber orientations, while others may not be the highest activation thresholds.

In some examples, Grade II activation area 122 may correspond to an activation area generated based on the third highest thresholds for each neuron representative. As another example, Grade II activation area 122 may correspond to an activation area generated based on the thresholds for each neuron representative for a 20 degree fiber orientation with respect to the Y-axis. In this example, the activation thresholds corresponding to neuron representatives having the 20 degree fiber orientation with respect to the Y-axis may have different rankings.

Grade III activation area 124 may correspond to an activation area generated based on the fifth highest thresholds for each neuron representative. As another example, Grade III activation area 124 may correspond to an area of activation generated based on the thresholds corresponding to a 40 degree fiber orientation with respect to the Y-axis for each of the neuron representatives. The display of multiple possible areas of activation for a selected set of therapy parameters may allow a user to make a selection of a set of therapy parameter values to use in providing electrical stimulation based on a range of possible areas of activation for a particular set of therapy parameter values. The actual neuron orientation in patient 12 may not be known. Thus, processor 80 that is configured to generate a display that includes plurality of activation areas that may result from delivery of electrical stimulation according to a particular set of therapy parameter values may help a user visualize the possible effects of the electrical stimulation according to the particular set of therapy parameter values.

Figure 14:
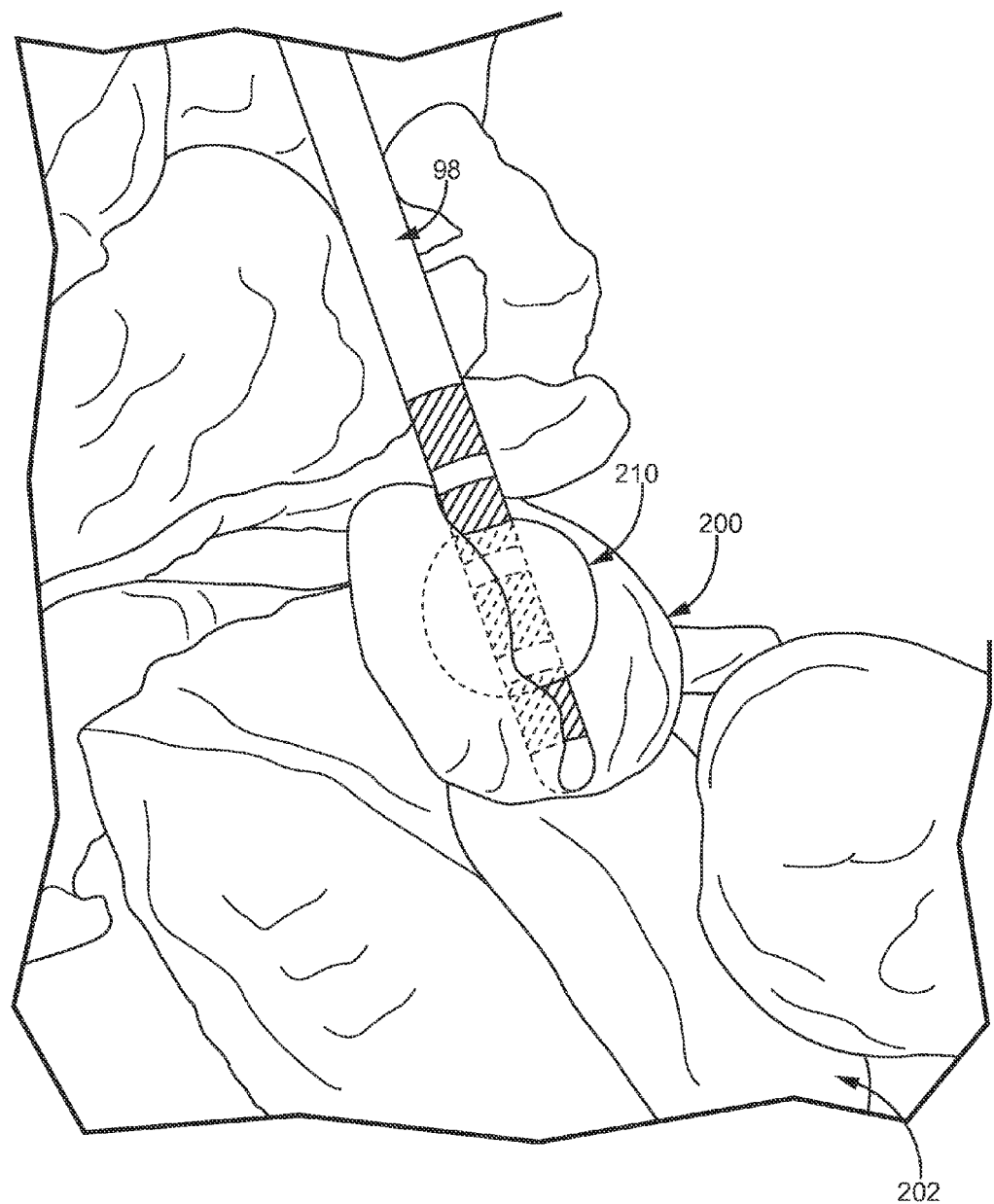
FIG. 14 is a conceptual diagram illustrating an example graphical user interface displaying an graphical representation of an activation area overlaying an graphical representation of a portion of a brain.

FIG. 14 is a conceptual diagram illustrating an example visualization provided via an example GUI generated by processor 80 in accordance with the present disclosure. The GUI shown in FIG. 14 includes lead representative 98, activation volume 210 and graphical representations of portions of a brain of patient 12. In particular, the GUI includes brain atlas structures, including the subthalamic nucleus 200 and the substantia nigra 202. The subthalamic nucleus 200 is a target tissue site for some deep brain stimulation therapies, such as therapy for the treatment of Parkinson's disease. By showing the activation area 210 overlapping brain atlas structures, a user may determine whether the activation area 110 covers the structure or other portion of the brain intended to be stimulated (referred to above as the "desired area"). The user may also visualize whether the simulation is activating areas outside a desired region, e.g., areas that may result in side effects.

FIG. 15 is a conceptual diagram illustrating the connection between the thresholds of various neuron representatives at different angles or fiber orientations. Fiber representative 126 is indicative of a fiber of a neuron rotated 0 degrees around the Y-axis relative to a longitudinal axis of lead representative 98, and corresponds to the neuron representative 134 in the upper right corner of the grid 132. Thus, fiber representative 126 is indicative of an orientation of a fiber of neuron representative 134. The longitudinal axis of lead representative 98 extends in the Z-axis direction. Grid 132 is the grid of neuron representatives in the Y-Z plane.

Fiber representative 128 is indicative of a fiber rotated 60° around the Y-axis relative to a longitudinal axis of lead representative 98 and running through neuron representative 134 in the upper right corner of grid 132. Fiber representative 128 also runs through neuron representative 136 on neuron representative grid 130. Thus, fiber representative 128 is indicative of an orientation of fibers of neuron representatives 130, 134. Grid 130 is a grid of neuron representatives rotated 60 degrees around the Y-axis. As shown in FIG. 15, neuron representative 134 and 136 have the same activation threshold if it is assumed that the threshold of the axon is the same along its length. The activation threshold assigned (e.g., by processor 80) to neuron representative 134 on the 2D grid in the Y-Z plane is assigned to neuron representative 136 in the rotated grid 130. In some examples, a plurality of neuron representatives for a 3D volume of tissue activation (not shown in FIG. 15) have the same activation thresholds. In some examples, processor 80 (or another processor) determining thresholds using the method of FIG. 8, for example, may not need to determine the activation threshold for each of the neuron representatives because of the relationship between neurons representatives as they are rotated around the Y-axis. For example, as shown in FIG. 15, and discussed above, fiber representative 128 runs through neuron representatives located at different positions within the grid as the grid is rotated around the Y-axis. Accordingly, in some examples where a 3D graphical representation is generated based on a plurality of 2D grids, the activation threshold for at least some of the neuron representatives may be determined based on the fiber orientation and a relationship between a neuron representative of a first one of the 2D grids and a second one of the 2D grids.

In various examples, a non-uniform grid of neuron representatives may be used to generate areas of activation with or without an indication of fiber orientation. In addition, a grid of neuron representatives used to generate areas of activation based on fiber orientation may include additional neuron representatives in areas of the neuron representative grid where there is a sharp change in activation threshold values (i.e., a non-uniform grid). In other examples, a grid of neuron representatives used to generate areas of activation based on fiber orientation may not include additional neuron representatives (i.e., a uniform grid).

The techniques described in this disclosure, including those attributed to IMD 16, programmer 14, or various constituent components may be implemented, at least in part, in hardware, software, firmware, or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, medical devices, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples of the disclosure have been described. These and other examples are within the scope of the following claims.

What is claimed is:

1. A method of generating an area of activation comprising:
    receiving, with one or more processors, a therapy delivery element selection, wherein the therapy delivery element selection corresponds to a therapy delivery element selected for implantation in a patient;
    receiving, with the one or more processors, a set of therapy parameter values, the set of therapy parameter values defining stimulation to be modeled;
    retrieving, from a memory, an area of activation look-up table based on the therapy delivery element selection, the area of activation look-up table comprising a neuron representative grid, wherein each neuron representative of the neuron representative grid is associated with a plurality of activation thresholds, each activation threshold of the plurality of activation thresholds being associated with a different angle of rotation around an axis, and wherein thresholds of the plurality of activation thresholds are organized into a plurality of activation threshold sets; and
    generating, with the one or more processors, a plurality of areas of activation based on the set of therapy parameter values, wherein each area of activation is generated based on a different activation threshold set of the plurality of activation threshold sets.

2. The method of claim 1, wherein each activation threshold set of the plurality of activation threshold sets comprises a single activation threshold for each neuron representative of the neuron representative grid.

3. The method of claim 1, further comprising:
    receiving, with the one or more processors, input indicating a therapy delivery element location, the therapy delivery element location corresponding to a location of desired therapy delivery element implantation; and
    selecting, from the memory, a brain atlas based on the therapy delivery element location.

4. The method of claim 3, further comprising:
    displaying the plurality of areas of activation and the brain atlas.

5. The method of claim 1, further comprising:
    ranking, with the one or more processors, the plurality of activation thresholds associated with each neuron representative from lowest to highest,
    wherein each activation threshold set comprises the activation thresholds of the same rank.

6. The method of claim 5, wherein the plurality of activation thresholds comprises activation thresholds associated with angles ranging from 0 to 90 degrees in increments of 10 degrees, and wherein the plurality of areas of activation are generated based on a first activation threshold set comprising the highest activation thresholds, a second activation threshold set comprising the third highest activation thresholds, and a third activation threshold set comprising the fifth highest activation thresholds.

7. The method of claim 5, wherein each of the activation thresholds of the plurality of activation thresholds is associated with a therapy parameter value.

8. The method of claim 1, wherein the set of therapy parameter values is a first set of therapy parameter values and the plurality of areas of activation is a first set of a plurality of areas of activation, the method further comprising:
    comparing the first set of the plurality of areas of activation to a desired area of tissue activation;
    adjusting the first set of therapy parameter values to create a second set of therapy parameter values based on the comparison; and
    generating a second set of a plurality of areas of activation based on the second set of therapy parameter values.

9. The method of claim 1, wherein the plurality of areas of activation correspond to at least one fiber orientation selected based on a diffusion tensor image of the patient.

10. The method of claim 1, wherein at least one of the areas of activation of the plurality of areas of activation is generated based on an interpolation between two activation threshold sets, and wherein each activation threshold set is associated with a different therapy parameter value and the interpolation is based on the therapy parameter value.

11. The method of claim 1, further comprising displaying the plurality of areas of activation.

12. The method of claim 1, wherein the set of therapy parameter values comprises an amplitude and a pulse width.

13. The method of claim 1, wherein the therapy delivery element selection comprises a lead and an electrode configuration.

14. A system comprising:
a memory configured to store a plurality of areas of activation look-up tables, the plurality of look-up tables being associated with a therapy delivery element selection; and
a processor configured to:
receive a therapy delivery element selection, wherein the therapy delivery element corresponds to a therapy delivery element selected for implantation in a patient,
receive a set of therapy parameters values,
retrieve, from the memory, an area of activation look-up table from the plurality of areas of activation look-up tables based on the therapy delivery element, wherein the area of activation look-up table comprises a neuron representative grid, and wherein each neuron representative of the neuron representative grid is associated with a plurality of activation thresholds, each activation threshold of the plurality of activation thresholds being associated with a different angle of rotation around an axis, and wherein the thresholds of the plurality of activation thresholds are organized into a plurality of activation threshold sets, and
generate a plurality of areas of activation based on the set of therapy parameter values, wherein each area of activation is generated based on a different activation threshold set of the plurality of activation threshold sets.

15. The system of claim 14, wherein each activation threshold set of the plurality of activation threshold sets comprises a single activation threshold for each neuron representative of the neuron representative grid.

16. The system of claim 14, wherein the processor is further configured to
receive a therapy delivery element location, the therapy delivery element location corresponding to a location of desired therapy delivery element implantation; and
select, from the memory, a brain atlas based on the therapy delivery element location.

17. The system of claim 16, further comprising a user interface configured to display the plurality of areas of activation and the brain atlas.

18. The system of claim 14, wherein the processor is further configured to rank the plurality of activation thresholds associated with each neuron representative from lowest to highest, and wherein each activation threshold set comprises the activation thresholds of the same rank.

19. The system of claim 18, wherein the plurality of activation thresholds comprises activation thresholds ranging from 0 to 90 degrees in increments of 10 degrees, and wherein the plurality of areas of activation are generated based on a first activation threshold set comprising the highest activation thresholds, a second activation threshold set comprising the third highest activation thresholds, and a third activation threshold set comprising the fifth highest activation thresholds.

20. The system of claim 18, wherein each of the activation thresholds of the plurality of activation thresholds is associated with a respective therapy parameter value.

21. The system of claim 14, wherein the set of therapy parameter values is a first set of therapy parameter values and the plurality of areas of activation is a first set of a plurality of areas of activation, further comprising comparing the first set of the plurality of areas of activation to a desired area of tissue activation, and wherein the processor is further configured to:
adjust the first set of therapy parameter values to create a second set of therapy parameter values based on the comparison; and
generate a second set of a plurality of areas of activation based on the second set of therapy parameter values.

22. The system of claim 14, wherein the plurality of areas of activation correspond to at least one fiber orientation selected based on a diffusion tensor imaging of the patient.

23. The system of claim 14, wherein the processor is further configured to generate at least one of the plurality of areas of activation based on an interpolation between two activation threshold sets, and wherein each activation threshold set is associated with a different therapy parameter value, and the interpolation is based on the therapy parameter.

24. A system comprising:
means for receiving a therapy delivery element selection, wherein the therapy delivery element selection corresponds to a therapy delivery element selected for implantation in a patient;
means for receiving a set of therapy parameters values;
means for retrieving, from a memory, an area of activation look-up table based on the therapy delivery element selection, wherein the area of activation look-up table comprises a neuron representative grid, and wherein each neuron representative of the neuron representative grid is associated with a plurality of activation thresholds, each of the plurality of activation thresholds associated with a different angle of rotation around an axis, and wherein the plurality of activation thresholds are organized into a plurality of activation threshold sets; and
means for generating a plurality of areas of activation based on the set of therapy parameters values, wherein each areas of activation is generated based on a different activation threshold set.

25. A non-transitory computer readable storage medium comprising a set of instructions, the set of instructions causing a programmable processor to:
receive a therapy delivery element selection, wherein the therapy delivery element selection corresponds to a therapy delivery element selected for implantation in a patient;
receive a set of therapy parameters;
retrieve, from a memory, an area of activation look-up table based on the therapy delivery element selection, wherein the area of activation look-up table comprises a neuron representative grid, and wherein each neuron representative of the neuron representative grid is associated with a plurality of activation thresholds, each of the plurality of activation thresholds associated with a different angle of rotation around an axis, and wherein the plurality of activation thresholds are organized into a plurality of activation threshold sets; and
generate a plurality of areas of activation based on the set of therapy parameters, wherein each area of activation is generated based on a different activation threshold set.

* * * * *